US012035989B2

(12) United States Patent
Clark et al.

(10) Patent No.: US 12,035,989 B2
(45) Date of Patent: Jul. 16, 2024

(54) SYSTEMS AND METHODS FOR A CONTROL STATION FOR ROBOTIC INTERVENTIONAL PROCEDURES USING A PLURALITY OF ELONGATED MEDICAL DEVICES

(71) Applicant: Corindus, Inc., Newton, MA (US)

(72) Inventors: Andrew Clark, Waltham, MA (US); Dino Kasvikis, Barrington, RI (US); Steven J. Blacker, Framingham, MA (US); Benjamin Hannon, Amesbury, MA (US); Max Ayers, Chicago, IL (US); Alix Dorfman, Somerville, MA (US)

(73) Assignee: Corindus, Inc., Newton, MA (US)

( * ) Notice: Subject to any disclaimer, the term of this patent is extended or adjusted under 35 U.S.C. 154(b) by 0 days.

(21) Appl. No.: 17/812,733

(22) Filed: Jul. 15, 2022

(65) Prior Publication Data
US 2023/0035508 A1   Feb. 2, 2023

Related U.S. Application Data

(60) Provisional application No. 63/203,845, filed on Aug. 2, 2021.

(51) Int. Cl.
*A61B 34/37* (2016.01)
*B25J 13/06* (2006.01)
*A61B 34/30* (2016.01)

(52) U.S. Cl.
CPC .............. *A61B 34/37* (2016.02); *B25J 13/06* (2013.01); *A61B 2034/301* (2016.02); *A61B 2034/303* (2016.02)

(58) Field of Classification Search
CPC .............. A61B 34/37; A61B 2034/301; A61B 2034/303; A61B 90/50; A61B 2090/374;
(Continued)

(56) References Cited

U.S. PATENT DOCUMENTS

| | | |
|---|---|---|
| 3,821,525 A | 6/1974 | Eaton et al. |
| 3,922,996 A | 12/1975 | Meyer |

(Continued)

FOREIGN PATENT DOCUMENTS

| | | |
|---|---|---|
| CN | 101427205 | 5/2009 |
| CN | 102124425 | 7/2011 |

(Continued)

OTHER PUBLICATIONS

PCT International Search Report and Written Opinion for PCT/US2017/031921; mail date Jul. 19, 2017; 9 pages.
(Continued)

*Primary Examiner* — Jason Holloway

(57) ABSTRACT

A system includes a robotic drive comprising a plurality of cassettes, each cassette to move an elongated medical device (EMD) loaded therein, and an input module to issue instructions to the robotic drive. The input module includes a first two or more selection buttons to select a first two or more EMDs loaded in respective ones of the plurality of cassettes, a first control actuatable to cause issuance of an instruction to the robotic drive to simultaneously move each of the first two or more EMDs linearly, and a second control actuatable to cause issuance of an instruction to the robotic drive to simultaneously rotate each of the first two or more EMDs.

19 Claims, 13 Drawing Sheets

(58) Field of Classification Search
CPC ........ A61B 2090/376; A61B 2090/571; A61B 34/25; A61B 34/74; A61B 2090/3762; A61B 2090/378; B25J 13/06
See application file for complete search history.

(56) References Cited

U.S. PATENT DOCUMENTS

| | | |
|---|---|---|
| 4,706,671 A | 11/1987 | Weinrib |
| 4,926,858 A | 5/1990 | Gifford et al. |
| 5,217,474 A | 6/1993 | Zacca et al. |
| 5,312,338 A | 5/1994 | Nelson et al. |
| 5,350,101 A | 9/1994 | Godlewski |
| 5,527,279 A | 6/1996 | Imran |
| 5,854,622 A | 12/1998 | Brannon |
| 5,907,487 A | 5/1999 | Rosenberg et al. |
| 6,590,171 B1 | 7/2003 | Wolf et al. |
| 7,331,967 B2 | 2/2008 | Lee et al. |
| 7,557,797 B2 | 7/2009 | Ludwig |
| 7,766,856 B2 | 8/2010 | Ferry et al. |
| 7,766,894 B2 | 8/2010 | Weitzner et al. |
| 7,972,298 B2 | 7/2011 | Wallace et al. |
| 8,052,636 B2 | 11/2011 | Moll et al. |
| 8,092,397 B2 | 1/2012 | Wallace et al. |
| 8,343,096 B2 | 1/2013 | Kirschenman et al. |
| 8,390,438 B2 | 3/2013 | Olson et al. |
| 8,617,102 B2 | 12/2013 | Moll et al. |
| 8,684,952 B2 | 4/2014 | Weitzner et al. |
| 8,736,212 B2 | 5/2014 | Sandhu et al. |
| 8,801,661 B2 | 8/2014 | Moll et al. |
| 9,198,714 B2 | 12/2015 | Worrell et al. |
| 9,220,568 B2 | 12/2015 | Bromander et al. |
| 9,283,046 B2 | 3/2016 | Walker et al. |
| 9,320,479 B2 | 4/2016 | Wenderow et al. |
| 9,326,822 B2 | 5/2016 | Lewis et al. |
| 9,408,669 B2 | 8/2016 | Kokish et al. |
| 9,566,414 B2 | 2/2017 | Wong et al. |
| 9,655,680 B2 | 5/2017 | Shim et al. |
| 9,713,500 B2 | 7/2017 | Kim et al. |
| 9,770,300 B2 | 9/2017 | Kwon et al. |
| 9,782,564 B2 | 10/2017 | Zirps et al. |
| 9,814,864 B2 | 11/2017 | Scarpine et al. |
| 9,825,455 B2 | 11/2017 | Sandhu et al. |
| 10,213,264 B2 | 2/2019 | Tanner et al. |
| 10,238,456 B2 | 3/2019 | Murphy et al. |
| 10,307,214 B2 | 6/2019 | Lathrop et al. |
| 2002/0177789 A1 | 11/2002 | Ferry et al. |
| 2004/0011154 A1 | 1/2004 | Dybro |
| 2004/0147934 A1 | 7/2004 | Kiester |
| 2004/0254566 A1 | 12/2004 | Plicchi et al. |
| 2005/0119615 A1 | 6/2005 | Noriega et al. |
| 2006/0074442 A1 | 4/2006 | Noriega et al. |
| 2006/0243080 A1 | 11/2006 | Takamoto et al. |
| 2007/0060879 A1 | 3/2007 | Weitzner et al. |
| 2008/0161801 A1 | 7/2008 | Steinke et al. |
| 2008/0243064 A1 | 10/2008 | Stahler et al. |
| 2009/0082722 A1 | 3/2009 | Munger et al. |
| 2009/0213073 A1 | 8/2009 | Obermeyer et al. |
| 2009/0248042 A1 | 10/2009 | Kirschenman |
| 2010/0010505 A1 | 1/2010 | Herlihy et al. |
| 2010/0175701 A1 | 7/2010 | Reis et al. |
| 2010/0274087 A1 | 10/2010 | Diolaiti et al. |
| 2011/0046441 A1* | 2/2011 | Wiltshire .............. A61B 1/313 600/104 |
| 2011/0237880 A1 | 9/2011 | Hamel et al. |
| 2012/0071752 A1 | 3/2012 | Sewell et al. |
| 2012/0001860 A1 | 6/2012 | Le |
| 2013/0172906 A1 | 7/2013 | Olsen et al. |
| 2014/0194897 A1 | 7/2014 | Kirschenman et al. |
| 2014/0276389 A1 | 9/2014 | Walker |
| 2014/0276646 A1* | 9/2014 | Wong .................... A61B 34/30 604/528 |
| 2014/0277002 A1 | 9/2014 | Grace |
| 2014/0277747 A1 | 9/2014 | Walker et al. |
| 2015/0142013 A1 | 5/2015 | Tanner et al. |
| 2015/0157497 A1 | 6/2015 | Hufford et al. |
| 2016/0184032 A1* | 6/2016 | Romo .................... B25J 9/1682 901/46 |
| 2016/0270780 A1 | 9/2016 | Hall et al. |
| 2017/0007343 A1 | 1/2017 | Yu |
| 2017/0119411 A1 | 5/2017 | Shah |
| 2017/0258538 A1* | 9/2017 | Cohen .................... A61B 17/28 |
| 2017/0348060 A1 | 12/2017 | Blacker |
| 2018/0325612 A1 | 11/2018 | Blacker et al. |
| 2018/0353247 A1 | 12/2018 | Ishihara et al. |
| 2019/0105110 A1* | 4/2019 | Tanner .................. A61B 34/71 |
| 2019/0175887 A1 | 6/2019 | Shameli |
| 2020/0155252 A1 | 5/2020 | Diolaiti et al. |
| 2020/0289228 A1 | 9/2020 | Denlinger et al. |
| 2021/0078080 A1 | 3/2021 | Mori et al. |

FOREIGN PATENT DOCUMENTS

| | | |
|---|---|---|
| CN | 102292692 | 12/2011 |
| EP | 0974889 | 1/2000 |
| EP | 2124800 | 12/2009 |
| EP | 2923669 | 6/2017 |
| JP | 200625300 | 9/2006 |
| JP | 2008515135 | 5/2008 |
| JP | 2015037572 | 2/2015 |
| JP | 2019505245 | 5/2017 |
| WO | 0161431 | 8/2001 |
| WO | 2003015428 | 12/2003 |
| WO | 2007005976 | 1/2007 |
| WO | 2010025338 | 3/2010 |
| WO | 2011094877 | 8/2011 |
| WO | 2021011518 | 1/2021 |
| WO | 2021011533 | 1/2021 |
| WO | 2021011551 | 1/2021 |
| WO | 2021011554 | 1/2021 |
| WO | 2021011571 | 1/2021 |
| WO | 2022154975 | 7/2022 |
| WO | 2022154976 | 7/2022 |
| WO | 2022154977 | 7/2022 |
| WO | 2022154978 | 7/2022 |
| WO | 2022154980 | 7/2022 |

OTHER PUBLICATIONS

Sato, et al., "Touche: Enhancing Tough Interaction on Humans, Screens, Liquids, and Everyday Objects," Chi' 12, May 5-10, 2012, Austin, Texas, USA, Copyright 2012 ACM 978-1-4503-1015-4/12/05, 10 pages.
European extended search report for EP 17820733.8; mail date Jan. 3, 2020; 9 pages.
EESR for EP Application 11833036.4; mail date Jun. 30, 2017; 12 pages.
International Preliminary Report on Patentability for PCT/US2011/053642; mail date Apr. 25, 2013; 12 pages.
International Search Report and Written Opinion for PCT/US2011/053642; mail date Jan. 17, 2012; 14 pages.
International Search Report for PCT/US2011/053642, mailed Jan. 17, 2012.
Auris Health, Inc. (2018). MONARCH Platform: User Manual.
European Search Report for Corresponding EP Application No. EP 22187460, dated Dec. 12, 2022.

\* cited by examiner

SYSTEMS AND METHODS FOR A CONTROL STATION FOR ROBOTIC INTERVENTIONAL PROCEDURES USING A PLURALITY OF ELONGATED MEDICAL DEVICES

CROSS-REFERENCE TO RELATED APPLICATIONS

The present application claims priority to U.S. Provisional Patent Application No. 63/203,845, filed Aug. 2, 2021, the contents of which are incorporated herein by reference for all purposes.

FIELD

Embodiments relate generally to the field of robotic medical procedure systems and, in particular, to systems, apparatus and methods for robotically controlling the movement of one or more elongated medical devices in robotic interventional medical procedures.

BACKGROUND

As used herein, the term elongated medical device (EMD) refers to, but is not limited to, catheters (e.g., guide catheters, microcatheters, balloon/stent catheters), wire-based devices (e.g., guidewires, embolization coils, stent retrievers, etc.), and medical devices comprising any combination of these. Wire-based devices include but are not limited to guidewires, microwires, proximal pushers for embolization coils, stent retrievers, self-expanding stents, and flow diverters. Typically, wire-based elongated medical devices (EMDs) do not have a hub or handle at their proximal terminal end.

Catheters and other EMDs may be used during minimally-invasive medical procedures for the diagnosis and/or treatment of diseases of various vascular systems, including neurovascular intervention (NVI) also known as neurointerventional surgery, percutaneous coronary intervention (PCI) and peripheral vascular intervention (PVI). These procedures typically involve navigating a guidewire through the vasculature and advancing a catheter into the vasculature via the guidewire to deliver therapy.

A catheterization procedure starts by gaining access into the appropriate vessel, such as an artery or vein, with an introducer sheath using standard percutaneous techniques. Through the introducer sheath, a sheath or guide catheter is then advanced over a diagnostic guidewire to a primary location such as an internal carotid artery for NVI, a coronary ostium for PCI, or a superficial femoral artery for PVI. A guidewire suitable for the vasculature is then navigated through the sheath or guide catheter to a target location in the vasculature. In certain situations, such as in the presence of tortuous anatomy, a support catheter or microcatheter is inserted over the guidewire to assist in navigating the guidewire.

A physician or operator may use an imaging system (e.g., a fluoroscope) to obtain a contrast-enhanced image for use as a roadmap of the vasculature to navigate the guidewire or catheter to the target location, for example, a lesion. Contrast-enhanced images are also obtained while the physician delivers the guidewire or catheter so that the physician can verify that the device is moving along the correct path to the target location. While observing the anatomy using fluoroscopy, the physician manipulates the proximal end of the guidewire or catheter to direct the distal tip into the appropriate vessels toward the lesion or target anatomical location and avoid advancing into side branches.

Robotic catheter-based procedure systems have been developed that may be used to aid a physician in performing catheterization procedures such as, for example, NVI, PCI and PVI. Examples of NVI procedures include coil embolization of aneurysms, liquid embolization of arteriovenous malformations and mechanical thrombectomy of large vessel occlusions in the setting of acute ischemic stroke. In an NVI procedure, the physician uses a robotic system to gain target lesion access by controlling the manipulation of a neurovascular guidewire and microcatheter to deliver the therapy to restore normal blood flow. Target access is enabled by the sheath or guide catheter but may also require an intermediate catheter for more distal territory or to provide adequate support for the microcatheter and guidewire. The distal tip of a guidewire is navigated into, or past, the lesion depending on the type of lesion and treatment. For treating aneurysms, the microcatheter is advanced into the lesion and the guidewire is removed and several embolization coils are deployed into the aneurysm through the microcatheter and used to block blood flow into the aneurysm. For treating arteriovenous malformations, a liquid embolic is injected into the malformation via a microcatheter. Mechanical thrombectomy to treat vessel occlusions can be achieved either through aspiration and/or use of a stent retriever. Depending on the location of the clot, aspiration is either done through an aspiration catheter, or through a microcatheter for smaller arteries. Once the aspiration catheter is at the lesion, negative pressure is applied to remove the clot through the catheter. Alternatively, the clot can be removed by deploying a stent retriever through the microcatheter. Once the clot has integrated into the stent retriever, the clot is retrieved by retracting the stent retriever and microcatheter (or intermediate catheter) into the guide catheter.

In PCI, the physician uses a robotic system to gain lesion access by manipulating a coronary guidewire to deliver the therapy and restore normal blood flow. The access is enabled by seating a guide catheter in a coronary ostium. The distal tip of the guidewire is navigated past the lesion and, for complex anatomies, a microcatheter may be used to provide adequate support for the guidewire. The blood flow is restored by delivering and deploying a stent or balloon at the lesion. The lesion may need preparation prior to stenting, by either delivering a balloon for pre-dilation of the lesion, or by performing atherectomy using, for example, a laser or rotational atherectomy catheter and a balloon over the guidewire. Diagnostic imaging and physiological measurements may be performed to determine appropriate therapy by using imaging catheters or fractional flow reserve (FFR) measurements.

In PVI, the physician uses a robotic system to deliver the therapy and restore blood flow with techniques similar to NVI. The distal tip of the guidewire is navigated past the lesion and a microcatheter may be used to provide adequate support for the guidewire for complex anatomies. The blood flow is restored by delivering and deploying a stent or balloon to the lesion. As with PCI, lesion preparation and diagnostic imaging may be used as well.

When support at the distal end of a catheter or guidewire is needed, for example, to navigate tortuous or calcified vasculature, to reach distal anatomical locations, or to cross hard lesions, an over-the-wire (OTW) catheter or coaxial system may be used. An OTW catheter includes a lumen for the guidewire that extends the full length of the catheter. This provides a relatively stable system because the guidewire is supported along the whole length. This system, however, has some disadvantages, including higher friction, and longer overall length compared to rapid-exchange catheters.

When performing vascular interventional procedures, the operator generally uses a set of controls provided at a control station in order to control the robotic system to move each catheter or wire as required. Each of the controls is typically configured to control a specific device, or to move the catheter or wire in a specific manner.

Such controls typically require an operator to depress and hold a device selection button with one digit while manipulating other controls with other digits. These simultaneous operations become difficult if not impossible as the number of EMDs under simultaneous control increases. For example, control of four different EMDs requires depression of corresponding selection buttons by all four digits of a hand.

The foregoing issue is exacerbated if continuous activation is employed. Continuous activation is a safety feature which requires an affirmative indication from an operator that motion is intended. This indication is typically provided via a digit-manipulated "deadman" switch, which must be depressed in order for EMD movement to occur and therefore requires simultaneous availability of yet another operator digit.

Physical challenges presented by conventional control stations may lead to difficulty in accurately controlling the movement and position of EMDs. Any unintended, accidental motion of an EMD may cause damage either to the patient or to the EMD.

Some systems include ergonomic hand grips on or adjacent to which controls are disposed. Although such hand grips may be attractive and comfortable to grip, the "home position" dictated by the grips limits the placement of controls to the immediate area which can be accessed by the digits while the hands rest on the grips. Otherwise, such systems require the operator to regularly release the grips and move one or both hands to access a control located elsewhere. Moreover, such systems are typically configured to favor a right-handed operator.

Systems are desired which provide precise and safe control of multiple EMDs during a robotic vascular intervention and which are intuitive, easy to use, and/or scalable.

BRIEF DESCRIPTION OF THE DRAWINGS

Embodiments will become more fully understood from the following detailed description, taken in conjunction with the accompanying drawings, wherein the reference numerals refer to like parts in which.

DETAILED DESCRIPTION

The following description is provided to enable any person in the art to make and use the described embodiments. Various modifications, however, will be readily-apparent to those in the art.

Some embodiments facilitate selection and simultaneous control of one or more (e.g., up to four) EMDs. By allowing one or more EMDs to be controlled simultaneously, without simultaneous depression of one or more device selection buttons, tasks can be more easily shared between hands, reducing load and strain. Moreover, continuous activation may be decoupled from EMD selection to increase ease of access and ease of use.

Embodiments may also provide position control (linear or rotational) and speed control, arranged in a manner so that each type of control is intuitively available to the operator via distinct control modalities (e.g., one type of control is provided via a scroll wheel and the other type of control is provided via a pair of buttons). Embodiments may provide linear movement of at least two devices in opposite directions simultaneously.

An input module according to some embodiments is less prescriptive than "grip-based" input modules regarding how the hands of an operator should be positioned. Since no specific "home position" is provided, movement of the hands over the controls of the input module may be more fluid than otherwise.

According to some embodiments, the controls of the input module are mirrored in arrangement and function between its left and right sides. Such an input module is equally usable by right-handed and left-handed operators. Moreover, such an arrangement may be inherently intuitive and associated with a shorter learning curve than alternative arrangements.

Some embodiments further facilitate prevention of EMD motions that might cause vascular damage, damage to the EMD or any other damage during a procedure. For example, some embodiments allow locking one or more EMDs such that the EMDs cannot move linearly regardless of any command initiated by the operator via the input module. Similarly, one or more EMDs may be also or alternatively locked such that the one or more EMDs cannot be rotated.

Figure 1:
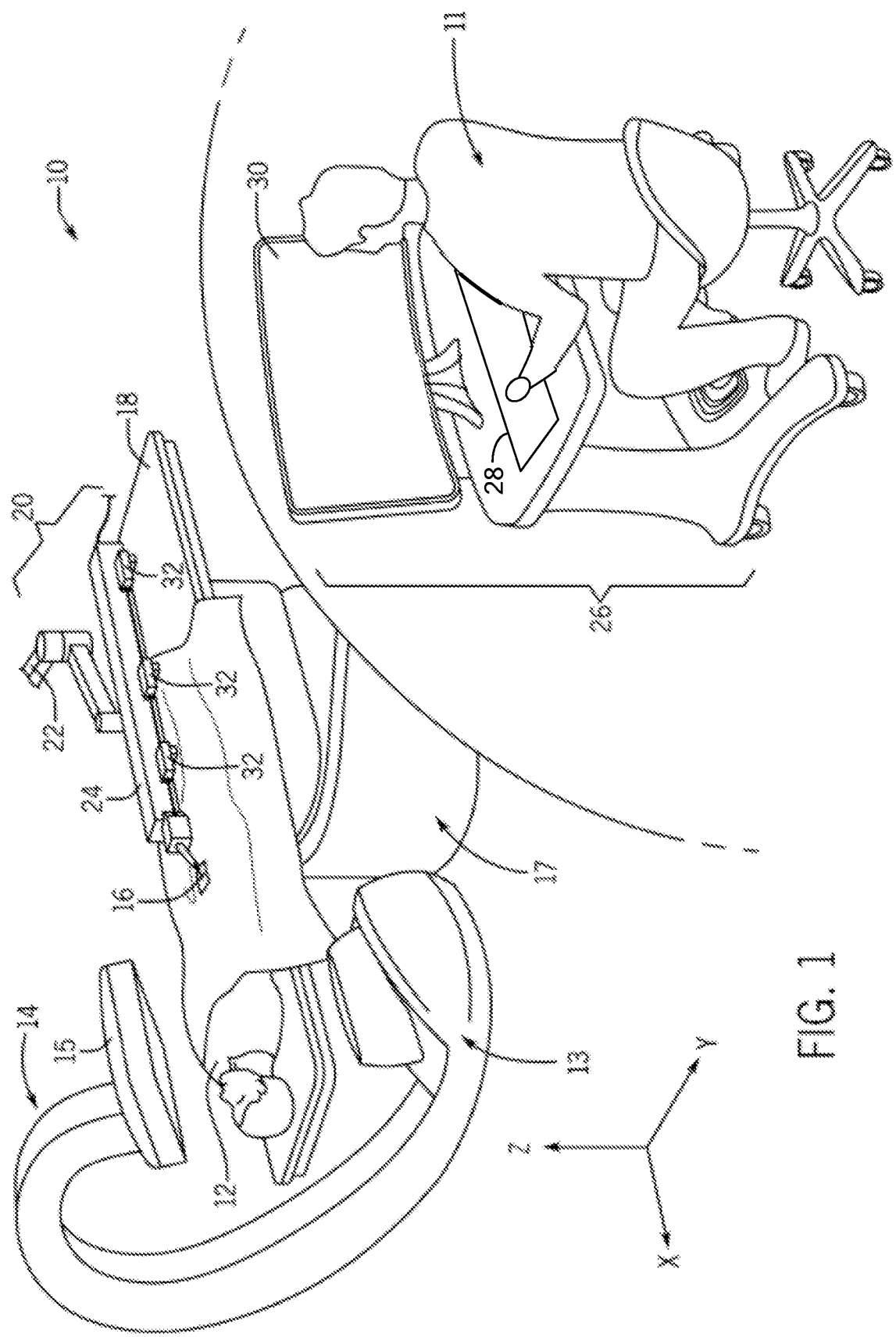
FIG. 1 is a perspective view of an exemplary catheter-based procedure system in accordance with some embodiments.

FIG. 1 is a perspective view of an exemplary catheter-based procedure system 10 in accordance with some embodiments. Catheter-based procedure system 10 may be used to perform catheter-based medical procedures, e.g., percutaneous intervention procedures such as a PCI (e.g., to treat STEMI), an NVI (e.g., to treat an emergent large vessel occlusion (ELVO)), and PVIs (e.g., for critical limb ischemia (CLI)). Catheter-based medical procedures may include diagnostic catheterization procedures during which one or more catheters or other elongated medical devices (EMDs) are used to aid in the diagnosis of a patient's disease. For example, during one embodiment of a catheter-based diagnostic procedure, a contrast media is injected into one or more arteries through a catheter and an image of the patient's vasculature is acquired while the contrast media resides therein.

Catheter-based medical procedures may also include catheter-based therapeutic procedures (e.g., angioplasty, stent placement, treatment of peripheral vascular disease, clot removal, arterial venous malformation therapy, treatment of aneurysm, etc.) during which a catheter (or other EMD) is used to treat a disease. Therapeutic procedures may be enhanced by the inclusion of adjunct devices 54 (shown in FIG. 2) such as, for example, intravascular ultrasound (IVUS), optical coherence tomography (OCT), fractional flow reserve (FFR), etc. It should be noted, however, that one in the art would recognize that certain specific percutaneous intervention devices or components (e.g., type of guidewire, type of catheter, etc.) may be selected based on the type of procedure that is to be performed. Catheter-based procedure system 10 can perform any number of catheter-based medical procedures with minor adjustments to accommodate the specific percutaneous intervention devices to be used in the procedures.

Catheter-based procedure system 10 includes, among other elements, a bedside unit 20 and a control station 26. Bedside unit 20 includes a robotic drive 24 and a positioning system 22 that are located adjacent to a patient 12. Patient 12 is supported on a patient table 18. The positioning system 22 is used to position and support the robotic drive 24. The positioning system 22 may be, for example, a robotic arm, an articulated arm, a holder, etc. The positioning system 22 may be attached at one end to, for example, a rail on the patient table 18, a base, or a cart. The other end of the positioning system 22 is attached to the robotic drive 24. The positioning system 22 may be moved out of the way (along with the robotic drive 24) to allow for the patient 12 to be placed on the patient table 18. Once the patient 12 is positioned on the patient table 18, the positioning system 22 may be used to situate or position the robotic drive 24 relative to the patient 12 for the procedure. In some embodiments, patient table 18 is operably supported by a pedestal 17, which is secured to the floor and/or earth. Patient table 18 is able to move with multiple degrees of freedom, for example, roll, pitch, and yaw, relative to the pedestal 17. Bedside unit 20 may also include controls and displays 46 (shown in FIG. 2). For example, controls and displays may be located on a housing of the robotic drive 24.

The term front will refer to the side of the robotic drive 24 that faces the patient 12 and away from the positioning system 22, while the term rear refers to the side of the robotic drive 24 that is closest to the positioning system 22. The terms top, up, and upper refer to the general direction away from the direction of gravity and the terms bottom, down, and lower refer to the general direction in the direction of gravity.

Generally, the robotic drive 24 may be equipped with the appropriate percutaneous interventional devices and accessories 48 (shown in FIG. 2) (e.g., guidewires, various types of catheters including balloon catheters, stent delivery systems, stent retrievers, embolization coils, liquid embolics, aspiration pumps, device to deliver contrast media, medicine, hemostasis valve adapters, syringes, stopcocks, inflation device, etc.) to allow the user or operator 11 to perform a catheter-based medical procedure via a robotic system by operating various controls of a control system as described herein such as the controls and input module located at the control station 26. Bedside unit 20, and in particular the robotic drive 24, may include any number and/or combination of components to provide bedside unit 20 with the functionality described herein. A user or operator 11 at control station 26 is referred to herein as the control station user, control station operator, user or operator. A user or operator at bedside unit 20 is referred to as bedside unit user, patient-side operator or bedside unit operator.

Figure 3:
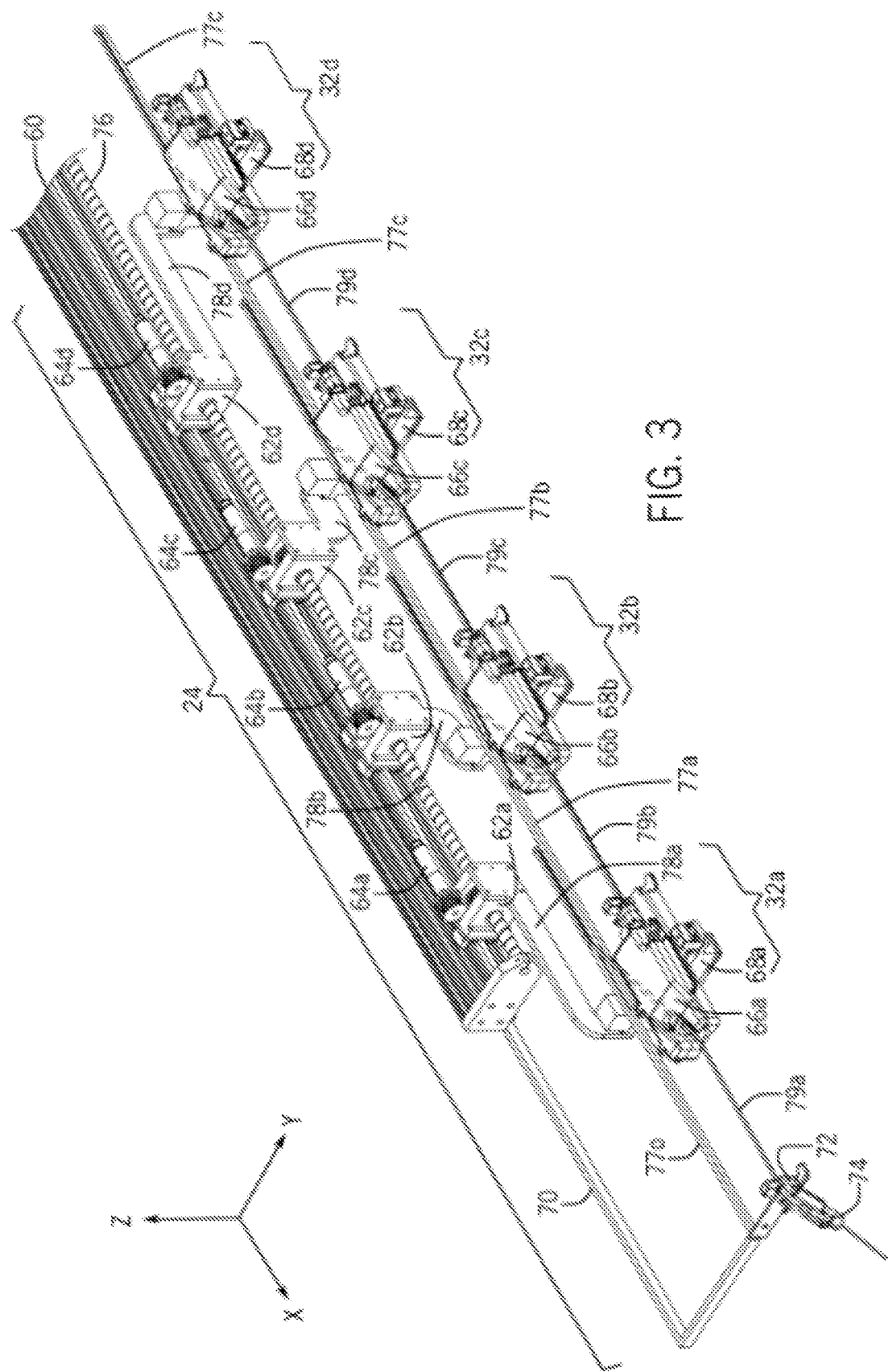
FIG. 3 is a perspective view of a robotic drive for a catheter-based procedure system in accordance with some embodiments.

The robotic drive 24 includes a plurality of device modules 32*a-d* mounted to a rail or linear member 60 (shown in FIG. 3). The rail or linear member 60 guides and supports the device modules. Each of the device modules 32*a-d* may be used to drive an EMD such as a catheter or guidewire. For example, the robotic drive 24 may be used to automatically feed a guidewire into a diagnostic catheter and into a guide catheter in an artery of the patient 12. One or more devices, such as an EMD, enter the body (e.g., a vessel) of the patient 12 at an insertion point 16 via, for example, an introducer sheath.

Bedside unit 20 is in communication with control station 26, allowing signals generated by the controls of control station 26 to be transmitted wirelessly or via hardwire to bedside unit 20 to control various functions of bedside unit 20, including functions of the robotic drive 24. As discussed below, control station 26 may include a control computing system 34 (shown in FIG. 2) or be coupled to the bedside unit 20 through a control computing system 34. Bedside unit 20 may also provide feedback signals (e.g., loads, speeds, operating conditions, warning signals, error codes, etc.) to control station 26, control computing system 34 (shown in FIG. 2), or both. Communication between the control computing system 34 and various components of the catheter-based procedure system 10 may be provided via a communication link that may be a wireless connection, cable connections, or any other means capable of allowing communication to occur between components.

The term local is used to refer to the location of the patient 12 and bedside unit 20. Catheter procedure system 10 may be operated by a control station 26 at the local site, a control station 26 at a remote site, or both a local control station 26 and a remote control station 26 at the same time. At a local site, user or operator 11 and control station 26 are located in the same room or an adjacent room to the patient 12 and bedside unit 20. As used herein, a local site is the location of the bedside unit 20 and a patient 12 or subject (e.g., animal or cadaver) and the remote site is the location of a user or operator 11 and a control station 26 used to control the bedside unit 20 remotely. The term remote is used to refer to locations that do not have physical access to the bedside unit 20 and/or patient 12 at a local site.

In some embodiments, the remote site and the local (patient) site are away from one another, for example, in different rooms in the same building, different buildings in the same city, different cities, or other different locations where the remote site does not have physical access to the bedside unit 20 and/or patient 12 at the local site.

Control station 26 includes input module 28 including controls configured according to some embodiments to receive user manipulations for controlling robotic drive 24 and/or various other components or systems of catheter-based procedure system 10. In the embodiment shown, control station 26 allows the user or operator 11 to control bedside unit 20 to perform a catheter-based medical procedure. For example, input module 28 may be configured to cause bedside unit 20 to perform various tasks using EMDs interfaced with the robotic drive 24 (e.g., to advance, retract, or rotate a guidewire, advance, retract or rotate a catheter, inflate or deflate a balloon located on a catheter, position and/or deploy a stent, position and/or deploy a stent retriever, position and/or deploy a coil, inject contrast media into a catheter, inject liquid embolics into a catheter, inject medicine or saline into a catheter, aspirate on a catheter, or to perform any other function that may be performed as part of a catheter-based medical procedure). Robotic drive 24 includes various drive mechanisms to cause movement (e.g., axial and rotational movement) of the components of the bedside unit 20 including the EMDs in response to user manipulation of the controls of input module 28.

An input module 28 may include device selection buttons as described below to allow the operator 11 to select which of the EMDs currently loaded into the robotic drive 24 are controlled via user manipulation of input controls of the input module 28. Automated move buttons may be used to enable algorithmic movements that the catheter-based procedure system 10 may perform on an EMD without direct command from the user or operator 11.

An input module 28 may also include a balloon or stent control that is configured to instruct inflation or deflation of a balloon and/or deployment of a stent. An input module 28 may include one or more buttons, scroll wheels, thumb knobs, joysticks, touch screen, etc. that is dedicated to instruct control of a particular component or components. In addition, one or more touch screens may display one or more icons (not shown) presenting relative positions of input modules 28 or various components of catheter-based procedure system 10. Such one or more touch screens may present a user interface for specifying and/or presenting a configuration of the controls of input module 28 and one or more functions, including but not limited to linear and/or rotational locking functions.

Control station 26 may include a display 30. In some embodiments, the control station 26 may include two or more displays 30. Display 30 may be configured to display information or patient specific data to the user or operator 11 located at control station 26. For example, display 30 may be configured to display image data (e.g., X-ray images, MRI images, CT images, ultrasound images, etc.), hemodynamic data (e.g., blood pressure, heart rate, etc.), patient record information (e.g., medical history, age, weight, etc.), lesion or treatment assessment data (e.g., IVUS, OCT, FFR, etc.). In addition, display 30 may be configured to display procedure specific information (e.g., procedural checklist, recommendations, duration of procedure, catheter or guidewire position, volume of medicine or contrast agent delivered, etc.). Further, display 30 may be configured to display information to provide the functionalities associated with control computing system 34 (shown in FIG. 2). Display 30 may include touch screen capabilities to provide some of the user input capabilities of the system.

Catheter-based procedure system 10 also includes an imaging system 14. Imaging system 14 may be any medical imaging system that may be used in conjunction with a catheter based medical procedure (e.g., non-digital X-ray, digital X-ray, CT, MRI, ultrasound, etc.). In an exemplary embodiment, imaging system 14 is a digital X-ray imaging device that is in communication with control station 26. In one embodiment, imaging system 14 may include a C-arm (shown in FIG. 1) that allows imaging system 14 to partially or completely rotate around patient 12 in order to obtain images at different angular positions relative to patient 12 (e.g., sagittal views, caudal views, anterior-posterior views, etc.). In one embodiment, imaging system 14 is a fluoroscopy system including a C-arm having an X-ray source 13 and a detector 15, also known as an image intensifier.

Imaging system 14 may be configured to acquire X-ray images of the appropriate area of patient 12 during a procedure. For example, imaging system 14 may be configured to acquire one or more X-ray images of the head to diagnose a neurovascular condition. Imaging system 14 may also be configured to take one or more X-ray images (e.g., real time images) during a catheter-based medical procedure to assist the operator 11 of control station 26 to properly position a guidewire, guide catheter, microcatheter, stent retriever, coil, stent, balloon, etc. during the procedure. The image or images may be displayed on display 30. For example, images may be displayed on display 30 to allow the user or operator 11 to accurately move a guide catheter or guidewire into the proper position.

In order to clarify directions, a rectangular coordinate system is introduced with X, Y, and Z axes. The positive X axis is oriented in a longitudinal (axial) distal direction, that is, in the direction from the proximal end to the distal end, stated another way from the proximal to distal direction. The Y and Z axes are in a transverse plane to the X axis, with the positive Z axis oriented up, that is, in the direction opposite of gravity, and the Y axis is automatically determined by right-hand rule.

Figure 2:
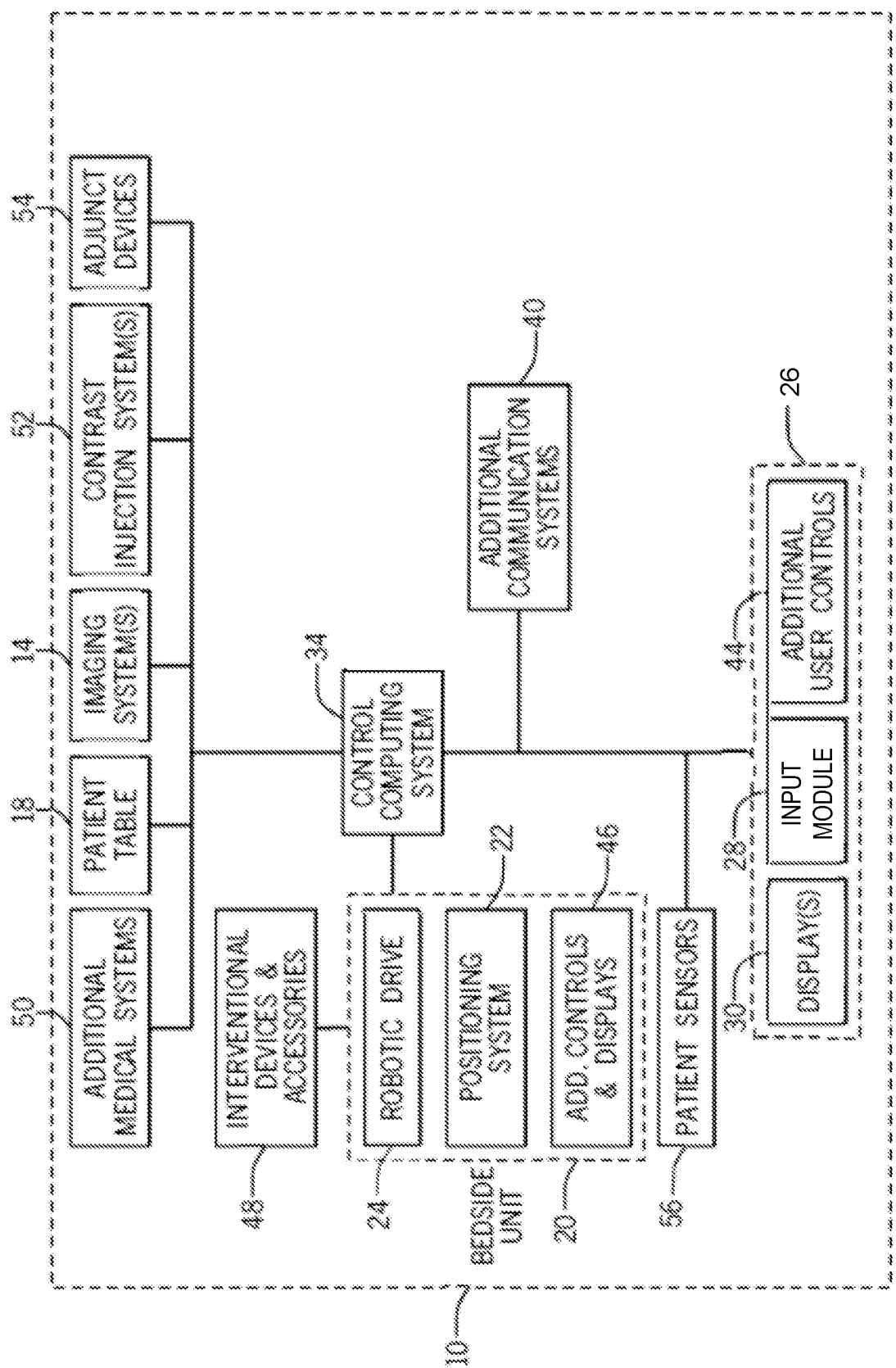
FIG. 2 is a schematic block diagram of an exemplary catheter-based procedure system in accordance with some embodiments.

FIG. 2 is a block diagram of catheter-based procedure system 10 in accordance with an exemplary embodiment. Catheter-procedure system 10 may include a control computing system 34. Control computing system 34 may physically be, for example, part of control station 26 (shown in FIG. 1). Control computing system 34 may generally comprise a computer processing unit suitable to provide catheter-based procedure system 10 with the various functionalities described herein. For example, control computing system 34 may be an embedded system, a dedicated circuit, a general-purpose system programmed with the functionality described herein, etc. Control computing system 34 is in communication with bedside unit 20, control station 38, additional communications systems 40 (e.g., a telepresence system, and patient sensors 56 (e.g., electrocardiogram (ECG) devices, electroencephalogram (EEG) devices, blood pressure monitors, temperature monitors, heart rate monitors, respiratory monitors, etc.).

Control computing system 34 is also in communication with imaging system 14, patient table 18, additional medical systems 50, contrast injection systems 52 and adjunct devices 54 (e.g., IVUS, OCT, FFR, etc.). The bedside unit 20 includes a robotic drive 24, a positioning system 22 and may include additional controls and displays 46. As mentioned above, the additional controls and displays may be located on a housing of the robotic drive 24. Interventional devices and accessories 48 (e.g., guidewires, catheters, etc.) interface to the bedside system 20. In some embodiments, interventional devices and accessories 48 may include specialized devices (e.g., IVUS catheter, OCT catheter, FFR wire, diagnostic catheter for contrast, etc.) which interface to their respective adjunct devices 54, namely, an IVUS system, an OCT system, and FFR system, etc.

In various embodiments, control computing system 34 is configured to receive and generate control signals based on user manipulation of the controls of input module 28 of control station 26, and/or based on information accessible to control computing system 34, such that a medical procedure may be performed using catheter-based procedure system 10.

Catheter-based procedure system 10 may be connected or configured to include any other systems and/or devices not explicitly shown. For example, catheter-based procedure system 10 may include image processing engines, data storage and archive systems, automatic balloon and/or stent inflation systems, medicine injection systems, medicine tracking and/or logging systems, user logs, encryption systems, systems to restrict access or use of catheter-based procedure system 10, etc.

FIG. 3 is a perspective view of a robotic drive 24 for a catheter-based procedure system 10 in accordance with some embodiments. Embodiments are not limited to the robotic drive 24 of FIG. 3. The robotic drive 24 of FIG. 3 includes multiple device modules 32*a-d* coupled to a linear member 60. Each device module 32*a-d* is coupled to the linear member 60 via a stage 62*a-d* moveably mounted to the linear member 60. A device module 32*a-d* may be connected to a stage 62*a-d* using a connector such as an offset bracket 78*a-d*. In another embodiment, the device module 32*a-d* is directly mounted to the stage 62*a-d*.

Each stage 62*a-d* may be independently actuated to move linearly along the linear member 60. Accordingly, each stage 62*a-d* (and the corresponding device module 32*a-d* coupled to the stage 62*a-d*) may independently move relative to each other and the linear member 60. A drive mechanism is used to actuate each stage 62*a-d*. In the embodiment shown in FIG. 3, the drive mechanism includes independent stage translation motors 64*a-d* coupled to each stage 62*a-d* and a stage drive mechanism 76, for example, a lead screw via a rotating nut, a rack via a pinion, a belt via a pinion or pulley, a chain via a sprocket, or the stage translation motors 64*a-d* may be linear motors themselves. In some embodiments, the stage drive mechanism 76 may be a combination of these mechanisms, for example, each stage 62*a-d* could employ a different type of stage drive mechanism. In some embodiments where the stage drive mechanism is a lead screw and rotating nut, the lead screw may be rotated and each stage 62*a-d* may engage and disengage from the lead screw to move, e.g., to advance or retract. In the embodiment shown in FIG. 3, the stages 62*a-d* and device modules 32*a-d* are in a serial drive configuration.

Each device module 32*a-d* includes a device module 68*a-d* and a cassette 66*a-d* mounted on and coupled to the device module 68*a-d*. In the embodiment shown in FIG. 3, each cassette 66*a-d* is mounted to the device module 68*a-d* in a vertical orientation. In other embodiments, each cassette 66*a-d* may be mounted to the device module 68*a-d* in other mounting orientations. Each cassette 66*a-d* is configured to interface with and support a proximal portion of an EMD (not shown). In addition, each cassette 66*a-d* may include elements to provide one or more degrees of freedom in addition to the linear motion provided by the actuation of the corresponding stage 62*a-d* to move linearly along the linear member 60. For example, the cassette 66*a-d* may include elements that may be used to rotate the EMD when the cassette is coupled to the device module 68*a-d*.

Each device module 68*a-d* includes at least one coupler to provide a drive interface to the mechanisms in each cassette 66*a-d* to provide the additional degree of freedom. Each cassette 66*a-d* also includes a channel in which a device support 79*a-d* is positioned, and each device support 79*a-d* is used to prevent an EMD from buckling. A support arm 77*a*, 77*b*, and 77*c* is attached to each device module 32*a*, 32*b*, and 32*c*, respectively, to provide a fixed point for support of a proximal end of the device supports 79*b*, 79*c*, and 79*d*, respectively. The robotic drive 24 may also include a device support connection 72 connected to a device support 79, a distal support arm 70 and a support arm 77*o*. Support arm 77*o* is used to provide a fixed point for support of the proximal end of the distal-most support arm 79*a* housed in the distal most device module 32*a*. In addition, an introducer interface support (redirector) 74 may be connected to the device support connection 72 and an EMD (e.g., an introducer sheath). The configuration of robotic drive 24 has the benefit of reducing volume and weight of the drive robotic drive 24 by using actuators on a single linear member.

To prevent contaminating the patient with pathogens, healthcare staff use aseptic technique in a room housing the bedside unit 20 and the patient 12 or subject (shown in FIG. 1). A room housing the bedside unit 20 and patient 12 may be, for example, a cath lab or an angio suite. Aseptic technique consists of using sterile barriers, sterile equipment, proper patient preparation, environmental controls and contact guidelines. Accordingly, all EMDs and interventional accessories are sterilized and can only be in contact with either sterile barriers or sterile equipment. In some embodiments, a sterile drape (not shown) is placed over the non-sterile robotic drive 24. Each cassette 66*a-d* is sterilized and acts as a sterile interface between the draped robotic drive 24 and at least one EMD. Each cassette 66*a-d* can be designed to be sterile for single use or to be re-sterilized in whole or part so that the cassette 66*a-d* or its components can be used in multiple procedures.

As used herein, the term cassette generally refers to a component of a robotic drive system including components to support and move (e.g., rotate and/or translate) at least one EMD. A device module generally refers to a component of a robotic drive system that includes one or more motors with drive couplers which interface with the EMD-moving elements of the cassette. A cassette may provide a sterile interface between at least one EMD and a device module directly or through a device adapter. The term drive module refers to the combination of a device module and a cassette.

In some embodiments, an EMD is a catheter having a hub at a proximal end of the catheter and a flexible shaft extending from the hub toward the distal end of the catheter, wherein the shaft is more flexible than the hub. In one embodiment the catheter includes an intermediary portion that transitions between the hub and the shaft that has an intermediate flexibility that is less rigid than the hub and more rigid than the shaft. In some embodiments the intermediary portion is a strain relief.

The longitudinal axis of a member (for example, an EMD or other element in the catheter-based procedure system) is the line or axis along the length of the member that passes through the center of the transverse cross section of the member in the direction from a proximal portion of the member to a distal portion of the member. For example, the longitudinal axis of a guidewire is the central axis in the direction from a proximal portion of the guidewire toward a distal portion of the guidewire even though the guidewire may be non-linear in the relevant portion.

Axial movement of a member refers to translation of the member along the longitudinal axis of the member. For example, when the distal end of an EMD is axially moved in a distal direction along its longitudinal axis into or further into the patient, the EMD is being advanced. When the distal end of an EMD is axially moved in a proximal direction along its longitudinal axis out of or further out of the patient, the EMD is being withdrawn.

In this regard, axial insertion refers to inserting a first member into a second member along the longitudinal axis of the second member. For example, an EMD that is axially loaded in a collet is axially inserted in the collet. An example of axial insertion could be referred to as back loading a catheter on the proximal end of a guidewire. Lateral insertion refers to inserting a first member into a second member along a direction in a plane perpendicular to the longitudinal axis of the second member. Lateral insertion can also be referred to as radial loading or side loading.

Rotational movement of a member refers to the change in angular orientation of the member about the local longitudinal axis of the member. For example, rotational movement of an EMD corresponds to clockwise or counterclockwise rotation of the EMD about its longitudinal axis due to an applied torque. Continuous motion refers to motion that does not require a reset and is uninterrupted, while discrete motion refers to motion that requires a reset and is interrupted.

The terms distal and proximal define relative locations of two different features. With respect to a robotic drive, the terms distal and proximal are defined by the position of the robotic drive in its intended use relative to a patient.

When used to define a relative position, the distal feature is the feature of the robotic drive that is closer to the patient than a proximal feature when the robotic drive is in its intended in-use position. Within a patient, any vasculature landmark further away along the path from the access point is considered more distal than a landmark closer to the access point, where the access point is the point at which the EMD enters the patient. Similarly, the proximal feature is the feature that is farther from the patient than the distal feature when the robotic drive in its intended in-use position.

When used to define direction, the distal direction refers to a path on which something is moving or is aimed to move or along which something is pointing or facing from a proximal feature toward a distal feature and/or patient when the robotic drive is in its intended in-use position. The proximal direction is the opposite direction of the distal direction. For example, referring to FIG. 1, a robotic device is shown from the viewpoint of an operator facing a patient. In this arrangement, the distal direction is along the positive X coordinate axis and the proximal direction is along the negative X coordinate axis.

With respect to movement of modules, and referring to FIG. 3, an EMD is moved in a distal direction on a path toward a patient through the introducer interface support 74 which defines the distal end of the robotic drive 24. The proximal end of the robotic drive 24 is the point furthest from the distal end along the negative X axis.

With respect to positions of the individual modules, and also referring to FIG. 3, the most distal device module is the device module 32*a* closest to the distal end of the robotic drive 24. The most proximal device module is the device module 32*d* positioned furthest from the distal end of the robotic drive 24 along the negative X axis. The relative position of device modules is determined by their relative location to the distal end of the robotic drive. For example, device module 32*b* is distal to device module 32*c*.

With respect to distal/proximal portions, sections or ends of an EMD or the robotic drive, the portions of cassette 66*a* and device module 68*a* are defined by their relative location to the distal end of the robotic drive. For example, the distal end of cassette 66*a* is the portion of the cassette that is closest to the distal end of the robotic drive and the proximal end of cassette 66*a* is the portion of the cassette that is furthest from the distal end of the robotic drive along the negative X axis when the cassette is in-use position on device module 68*a*. Stated in another way, the distal end of cassette 66*a* is the portion of the cassette through which an EMD is closest to the path leading to a patient in the in-use position.

As previously discussed, embodiments of a control station 26 can include a variety of different input modules for controlling the bedside unit 20. Input modules can include a variety of different input controls (for example, buttons, scroll wheels, knobs, joysticks) that can be manipulated by a user to control (or, instruct) operation of the robotic drive 24. These input controls can be arranged in different layouts or patterns on the input module to facilitate desired functions and cooperative sequencing thereof to perform a desired task requiring independent (and sometimes simultaneous) movement of multiple EMDs.

Additionally, embodiments of an input module can be configured to operate in a variety of different control modes. The functions assigned to one or more controls of an input module in a first control mode may differ from the functions assigned to the one or more controls in a second control mode, and control modes may be selected based on the procedure being performed, the device or devices to be controlled, user preferences, or any other factors. The input module can be configured to switch between different control modes in response to input from the user or the control computing system 34.

An input module as described herein may be fixed to, integrated with, or simply rested atop a surface of the control station 26. As described herein, an input module may comprise a single integrated housing or multiple independently-movable housings. An input module may be rectangular, substantially rectangular (e.g., rectangular with rounded edges) or other similar shapes. An input module may be roughly two times wider than taller. In one embodiment, an input module is roughly 200 mm tall and 413 mm wide. In another embodiment, an input module is roughly 300 mm tall and 620 mm wide. In yet another embodiment, an input module is roughly 238 mm tall by roughly 492 mm wide.

Figure 4:
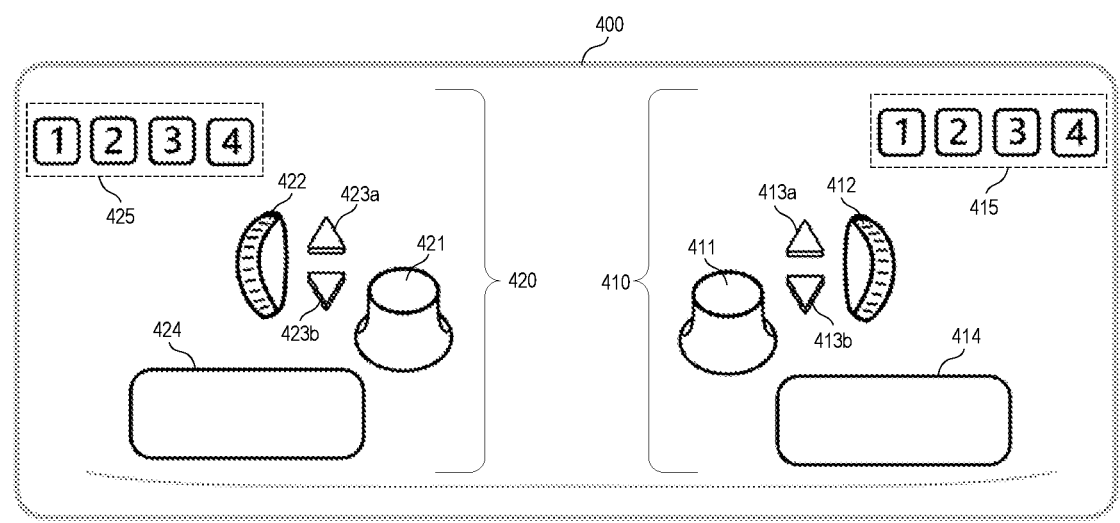
FIG. 4 is a view of an input module for a catheter-based procedure system in accordance with some embodiments.

FIG. 4 is a view of input module 400 for controlling a robotic drive of a catheter-based procedure system in accordance with some embodiments. Input module 400 may facilitate simultaneous selection and control of one or more EMDs.

Each of knobs 411, 421 may comprise a protrusion that extends upward from the flat base of input module 400. The protrusion may be round or substantially round. Each knob 411, 421 may be wider at the base than at the top so as to define a "skirt" on which an operator's thumb may engage the knob during rotation thereof. Knobs 411, 421 may be located "centrally" with respect to buttons 415 and 425 and buttons 414 and 424.

Buttons 413*a* and 413*b* and buttons 423*a* and 423*b* may comprise a protrusion that extends upward from the flat base. Buttons 413*a* and 413*b* and buttons 423*a* and 423*b* may extend upward from the base to a lesser degree than knobs 411 and 421. Buttons 413*a* and 413*b* and buttons 423*a* and 423*b* may be triangular, but also may be other shapes such as square, rectangular, oval, circular, etc. Buttons 413*a* and 413*b* may be implemented using a single button capable of receiving two or more different inputs (e.g., a rocker button), and buttons 423*a* and 423*b* may also be implemented using such a single button. For example, buttons 413*a* and 413*b* may be implemented using a single button with one depressable end corresponding to button 413a and the other depressable end corresponding to button 413b. Buttons 413a and 413b and buttons 423a and 423b may be parallel or substantially parallel to one other or may be arranged at an angle. Buttons 413a and 413b and buttons 423a and 423b may be located "centrally" with respect to buttons 415 and 425 and buttons 414 and 424.

Continuous activation buttons 414 and 424 may be substantially rectangular, as shown, rectangular, oval, circular or square. Continuous activation buttons 414 and 424 may be located closer to an operator during operation than all other buttons and controls of 400. Continuous activation buttons 414 and 424 may protrude from the base of module 400 or may be substantially contiguous with a surface of module 400. Continuous activation buttons 414 and 424 may be smooth or include textured portions such as dimples. Continuous activation buttons 414 and 424 could be physical buttons that deflect/translate when actuated (e.g., depressed), or solid-state buttons such as a capacitive touch panel or a piezoelectric device which are actuated by touch and do not noticeably "travel" when so activated.

Buttons 415 and 425 may be square, as shown, or may be other shapes such as circles, rectangles, ovals, etc. Buttons 415 and 425 may be located farther away from an operator during operation than all other buttons of module 400. Buttons 415 and 425 may protrude from the base or be substantially contiguous therewith. Buttons 415 and 425 may be smooth or include raised portions such as dimples. The raised portions of various buttons 415 and 425 may differ from one another to assist an operator in distinguishing a button by touch alone.

Controls 412, 422 may be round, as shown. In the embodiment shown in FIG. 4, controls 412, 422 are wheels. Controls 412, 422 include tactile elements to improve grip and to help an operator "find" these controls while not looking at the input module 400. In other embodiments, controls 412, 422 may be smooth. Controls 412, 422 may be arranged parallel or substantially parallel to one another. Controls 412, 422 may be located "centrally" on input module 400 with respect to buttons 415, 425, 414 and 424.

Input module 400 may be substantially flat over its entire surface or may comprise different elevations. For example, some portions of its surface may be raised with respect to others or may be lower with respect to others. A change in elevation may be gradual or sudden.

Using right-side controls 410 as exemplary, an operator may actuate knob 411 by placing a right thumb on a side portion (e.g., a skirt) of knob 411 and using the thumb to bias knob 411 in a clockwise or counterclockwise direction so as to rotate knob 411. This actuation causes issuance of an instruction to robotic drive 24 to rotate the one or more EMDs which are currently selected by right-side controls 410 as will be described below.

An operator may actuate scroll wheel 412 to cause issuance of an instruction to robotic drive 24 to change a linear position of the one or more EMDs selected by right-side controls 410, and may actuate buttons 413a and 413b to cause issuance of an instruction to robotic drive 24 to move the one or more EMDs selected by right-side controls 410 linearly (in respective opposite directions) and at a constant speed. Buttons 413a and 413b may provide analog (or simulated analog) functionality in that the constant speed is dependent on the degree to which a button is depressed. In a case that buttons 413a and 413b are implemented by a single rocker switch, the constant speed may be determined by how far the switch is tilted toward one of its opposing positions. The linear and rotational movement mentioned above is subject to any software-based locking settings which may be currently active, as will be described below.

According to some embodiments, actuation of any of controls 411, 412, 413a and 413b does not cause issuance of an instruction to robotic drive 24 unless continuous activation button 414 is actuated (e.g., depressed) simultaneously with such actuation. In this regard, embodiments include many possible implementations for issuing an instruction to robotic drive 24 due to activation of an input module control. In one example, one or more computing systems (e.g., control computing system 34) are intermediate to input module 400 and robotic drive 24. The one or more computing systems receive signals from input module 400 and issue corresponding instructions to robotic drive 24 based on the received signals. In one example, actuation of knob 411 while button 414 is not actuated results in no signal being output from input module 400 to the one or more computing systems and therefore no instruction being issued to robotic drive 24.

In another example, actuation of knob 411 while button 414 is not actuated causes input module 400 to output one or more signals representing the actuation of button 414 (e.g., the degree to which knob 411 was rotated) and indicating that button 414 is not actuated. The one or more intermediate computing systems determine, based on the one or more signals, not to issue an instruction to robotic drive 24. In some embodiments, the one or more computing systems further determine to present a message to the operator indicating that the rotation of knob 411 is detected but no corresponding EMD rotation is occurring.

Similarly, actuation of knob 411 while button 414 is actuated causes input module 400 to output one or more signals representing the actuation of button 414 and indicating that button 414 is actuated. Based on these one or more signals, the one or more intermediate computing systems issue an instruction to robotic drive 24 to rotate the one or more EMDs currently selected by buttons 415.

Actuation of knob 411 may comprise rotation and/or depression of knob 411. Actuation of scroll wheel 412 may comprise rolling wheel 412 clockwise or counter-clockwise, and actuation of buttons 413a, 413b may comprise depression thereof. An operator may perform each of these actuations using a thumb, a finger or a combination of a thumb and finger, for example.

In one example, an operator positions a right hand such that a heel of the palm is positioned to selectively actuate button 414, the right thumb is positioned to selectively actuate knob 411 and the index finger and/or middle finger are positioned to selectively actuate scroll wheel 412, buttons 413a, or button 413b. Rotation of knob 411 using the right thumb may be facilitated by biasing the thumb against the substantially vertical surface of knob 411 or the wider skirt portion, either of which may be textured to facilitate this biasing. Knob 411 may also be rotated by pinching/grasping using multiple digits. Button 414 may be sized and positioned to allow hands of many different sizes to comfortably maintain the above-described position.

Right-side selection buttons 415 may be actuated to select one or more EMDs to be moved based on instructions issued in response to manipulation of right-side controls 411, 412, 413a, 413b and 414. Selection buttons 415 labeled 1, 2, 3 and 4 may be used to select, respectively, an EMD which is supported by a first cassette, an EMD which is supported by a second cassette, an EMD which is supported by a third cassette, and an EMD which is supported by a fourth cassette. Advantageously, selection buttons 415 may be used to simultaneously select more than one EMD at a given time (which may then be simultaneously controlled using right-side controls 411, 412, 413a, 413b and 414), and do not need to be continuously depressed by an operator to maintain such selection.

In this example, pressing and release of any of selection buttons 415 results in selection of an associated EMD. Consequently, the EMDs of cassettes 1 and 3 may be selected by pressing and releasing button 1 and then pressing and releasing button 3. Simultaneously pressing and releasing button 1 and button 3 may also result in selection of the EMDs of cassettes 1 and 3.

According to some embodiments, selection of a button 415 corresponding to an already-selected EMD does not affect the selection of EMDs. That is, buttons 415 can only be used to select an EMD and not to de-select an EMD. Such an embodiment may include an additional control within controls 410 and 420 which may be actuated to deselect all EMDs which are currently selected by corresponding controls 415 or 425.

In other embodiments, selection of a button 415 corresponding to an already-selected EMD causes de-selection of the EMD. In still other embodiments, selecting any button 415 causes removal of all previous selections and selection of the EMD corresponding to the selected button 415. In order to select multiple EMDs in such a case, the selection buttons 415 associated with each of the multiple EMDs are depressed simultaneously for a threshold time period (e.g., 20-50 ms).

Right-side controls 410 and left-side controls 420 are substantially mirror images of one another, with the exception of selection buttons 415 and 425. The respective left-to-right orders of selection buttons 415 and 425 are consistent with the arrangement of the actual modules of robotic drive 24 and the display of those modules on the below-described user interface. Each of left-side controls 420 may be implemented substantially identically to their similarly-numbered counterparts of right-side controls 410.

While the right hand is positioned with respect to controls 410 as described above, an operator may position a left hand such that a heel of the palm is positioned to selectively actuate button 424, the left thumb is positioned to selectively actuate knob 421 and the left index finger and/or middle finger are positioned to selectively actuate scroll wheel 422, buttons 423a, or button 423b. Other operator hand positions are also expected. For example, an operator may place their right index finger on right wheel 412 and their left hand on right knob 412. Input module 400 allows simultaneous selection of one or more EMDs for each of the right-side controls 410 and left-side controls 420. Right-side controls 410 may then be used to simultaneously control rotation or linear movement of the EMDs selected for right-side controls 410, and left-side controls 420 may then be used to simultaneously control rotation or linear movement of the EMDs selected for left-side controls 420.

Embodiments may implement any suitable logic to resolve conflicting selections of EMDs between selection buttons 415 and 425. For example, it is assumed that button 2 of selection buttons 415 and button 1 of selection buttons 425 are selected. Next, the operator depresses button 1 of selection buttons 415. In some embodiments, this action results in de-selection of button 2 and selection of button 1 of selection buttons 415 and de-selection of button 1 of selection buttons 425.

In another example, it is assumed that button 3 of selection buttons 415 and buttons 1 and 2 of selection buttons 425 are selected. The operator then depresses button 1 of selection buttons 415. In some embodiments, this action results in de-selection of button 3 of selection buttons 415 and button 1 of selection buttons 425 and selection of button 1 of selection buttons 415, leaving button 2 of selection buttons 425 also selected. In other embodiments, the action results in de-selection of button 3 of selection buttons 415 and buttons 1 and 2 of selection buttons 425 and selection of button 1 of selection buttons 415.

It is assumed in some embodiments that an EMD moves only if selected and if an instruction to move the EMD is currently being issued to robotic drive 24. The proximal ends of all other EMDs mounted within robotic drive 24 remain stationary, due to internal friction, active braking, and/or other mechanisms of robotic drive 24.

Figure 5A:
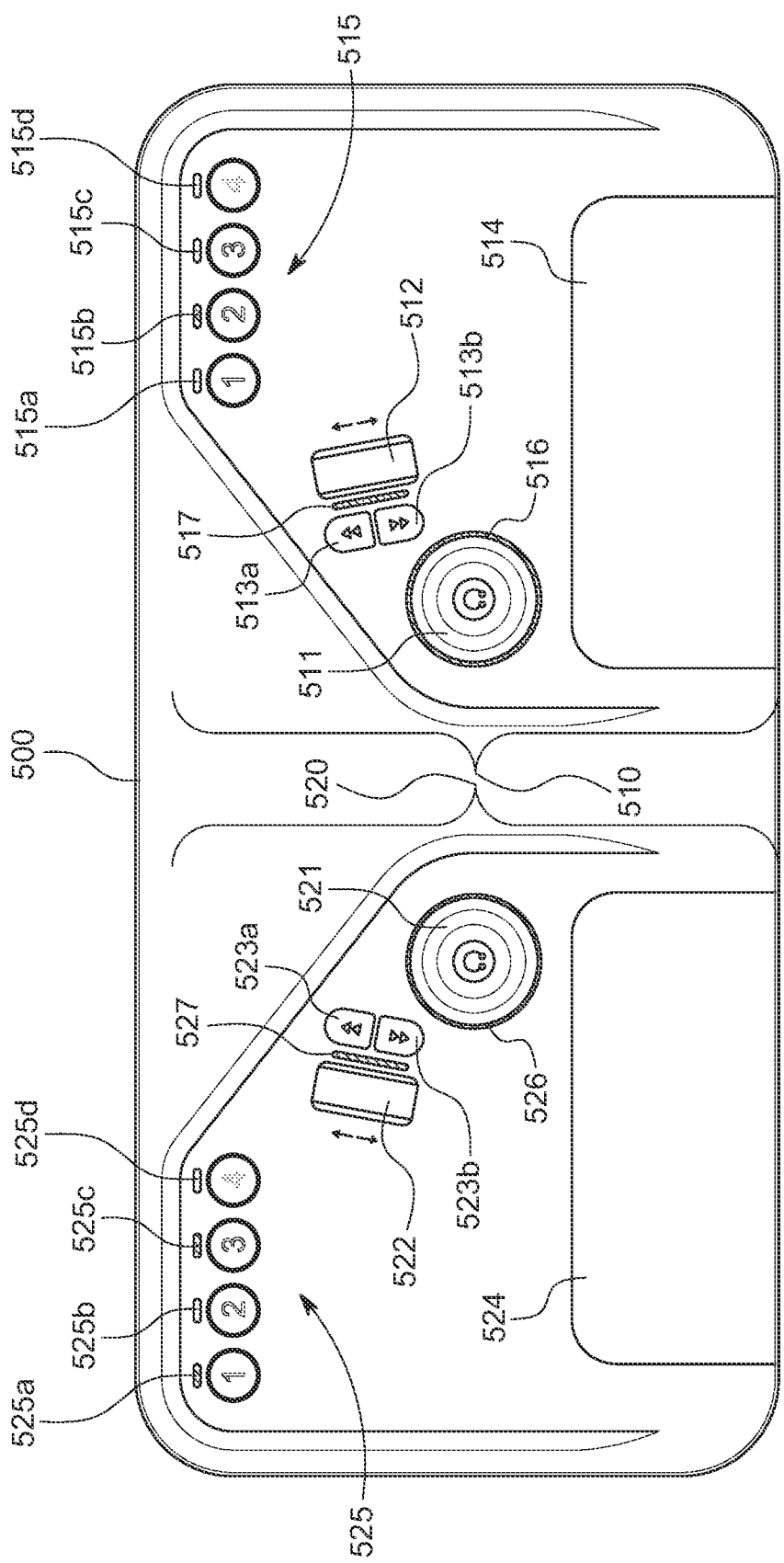
FIG. 5A is a view of an input module for a catheter-based procedure system in accordance with some embodiments.
Figure 5B:
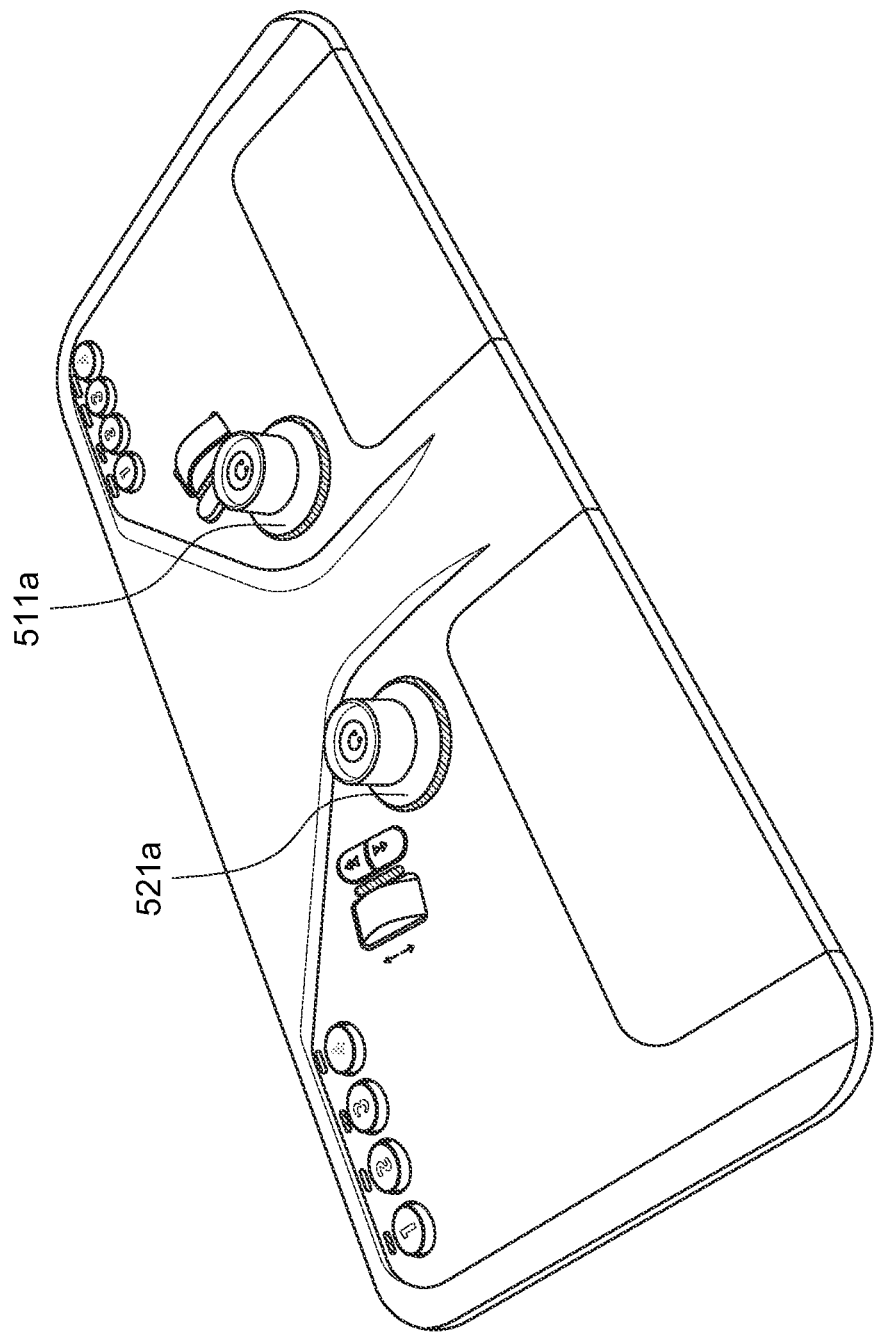
FIG. 5B is a view of an input module for a catheter-based procedure system in accordance with some embodiments.

FIGS. 5A and 5B are views of input module 500 according to some embodiments. Input module 500 includes right-side controls 510 and left-side controls 520, which may be implemented generally as described above with respect to similarly-numbered controls of input module 400. As shown, the surface to which the controls are mounted is substantially flat. The flatness may serve to increase the freedom with which an operator's hands move about the controls of input module 500. Moreover, the mirroring of the layout and operation of the controls equally favors right-handed and left-handed operators and is more intuitive than other arrangements.

Each of knobs 511 and 521 may comprise a round or substantially round protrusion that extends upward from the flat base of input module 500. Each knob 511, 521 may include an integrated skirt (511a, 521a of FIG. 5B) on which an operator's thumb may engage the knob during rotation thereof. Skirts 511a and 521a may include tactile surfaces to facilitate location and movement thereof. Knobs 511 and 521 may be located "centrally" with respect to buttons 515, 525, 514 and 524.

Each of buttons 513a, 513b, 523a and 523b may comprise a protrusion that extends upward from the base of module 500. Buttons 513a, 513b, 523a and 523b may extend upward from the base to a lesser degree than knobs 511 and 521. Buttons 513a, 513b, 523a and 523b may be triangular or any other shapes such as square, rectangular, oval, circular, etc.

Buttons 513a and 513b may be implemented using a single button capable of receiving two or more different inputs (e.g., a rocker button), and buttons 523a and 523b may also be implemented using such a single button. For example, buttons 513a and 513b may be implemented using a single button with one depressable end corresponding to button 513a and the other depressable end corresponding to button 513b. Buttons 513a, 513b, 523a and 523b may be parallel or substantially parallel to one other or may be arranged at an angle. Buttons 513a, 513b, 523a and 523b may be located "centrally" with respect to buttons 515, 525, 514 and 524.

Continuous activation buttons 514 and 524 may be substantially rectangular, as shown, rectangular, oval, circular or square. Continuous activation buttons 514 and 524 may be closer to an operator during operation than all other buttons and controls of module 500. Continuous activation buttons 514 and 524 may protrude from the base of module 500 or may be substantially flat and contiguous with the base of module 500.

Continuous activation buttons 514 and 524 may be smooth or textured (e.g., comprising raised portions such as dimples). Continuous activation buttons 514 and 524 may be physical buttons that deflect/translate when actuated, or solid-state buttons such as a capacitive touch panel or a piezoelectric device which are actuated by touch and do not noticeably "travel" when so activated.

Buttons 515 and 525 may be round, as shown, or may be other shapes such as squares, rectangles, ovals, etc. Buttons 515 and 525 may be located farther away from an operator during operation than all other buttons of module 500. Buttons 515 and 525 may protrude from the base of module 500 or be substantially contiguous therewith. Buttons 515 and 525 may be smooth or include raised portions such as dimples. The raised portions of various buttons 515 and 525 may differ from one another to assist an operator in distinguishing a button by touch alone.

In the embodiment shown in FIGS. 5A and 5B, controls 512 and 522 are wheels. Controls 512 and 522 may include tactile elements to improve grip and to help an operator "find" these controls while not looking at the input module 500. In other embodiments, controls 512 and 522 are smooth. Controls 512 and 522 may be arranged parallel or substantially parallel to one another. Controls 512 and 522 may be located "centrally" on input module 500 with respect to buttons 515, 525, 514 and 524.

Buttons 513*a*, 513*b*, 523*a*, 523*b* and scroll wheels 512 and 522 are angled for ergonomic considerations to reduce wrist ulnar deviation. Such angling may allow operator hand placement similar to that when using a computer keyboard.

Input module 500 may be substantially flat over its entire surface or may comprise different elevations. For example, some portions of the surface may be raised with respect to others or may be lower with respect to others. A change in elevation may be gradual or sudden. For example, the embodiment shown in FIGS. 5A and 5B comprises a gradual depression separating controls 510 and 520. The depression has a "funnel" shape comprised of a triangle and rectangle. The triangular portion may be "steeper" than the rectangular portion where the rectangular portion generally becomes less steep with respect to the surface of the base of module 500.

Selection buttons 515 and 525 may be opaque buttons with backlit digits. The digit of a selection button is backlit only if the corresponding cassette is selectable (e.g., after the operator indicates, via a user interface as described below, that the cassette has been loaded with an EMD) and is not backlit when the cassette is not selectable. If a cassette is not selectable, neither the corresponding selection button of buttons 515 nor the corresponding selection button of buttons 525 are backlit (e.g., button 4 of buttons 515 and of buttons 525).

Indicators 515*a*-515*d* and 525*a*-525*d* indicate which of buttons 515 and 525 are currently selected. Indicators may be various shapes including "pill"-shaped, "eyebrow"-shaped, rectangles, circles, squares, etc. In some embodiments, indicators 515*a*-515*d* and 525*a*-525*d* are lights and are lit when a corresponding button (and cassette) is selected and are off when not selected. Since a cassette may only be selected for control using right-side controls 510 or left-side controls 520, but not both, a selection button 515 which is indicated as selected by one of indicators 515*a*-515*d* (e.g., selection button 2) is not indicated as selected by the corresponding one of indicators 525*a*-525*d*.

Indicators 516 and 517 may selectively depict one of three different states of controls 511, 512, 513*a* and 513*b*. In a first state, the controls are disabled and cannot be used control an EMD. The first state may be employed while a bedside control station is controlling the EMDs, while an EMD is being inserted into a cassette, etc. A second state indicates that the controls are enabled but button 514 is not depressed. Accordingly, while in the second state, manipulation of controls 511, 512, 513*a* and 513*b* will not result in EMD movement. The third state exists when the controls are enabled and button 514 is depressed. In the third state, manipulation of controls 511, 512, 513*a* and 513*b* will result in the transmission of instructions to move the one or more EMDs which are currently selected via selection buttons 515 as described above.

Indicators 526 and 527 may selectively depict the states of controls 521, 522, 523*a* and 523*b*, which are independent of the states of controls 511, 512, 513*a* and 513*b*. For example, indicators 516 and 517 may indicate the second state (because button 514 is not actuated) while indicators 526 and 527 indicate the third state (because button 524 is actuated). According to some embodiments, indicators 516, 517, 526 and 527 are lights and are off to indicate the first state, are a first color (e.g., white) to indicate the second state, and are a second color (e.g., orange) to indicate the third state.

Figure 6:
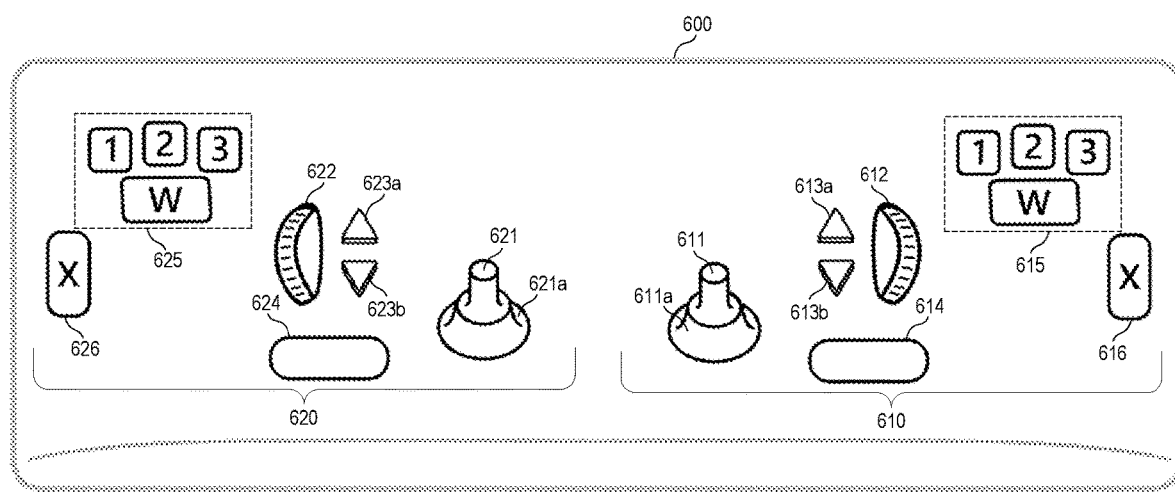
FIG. 6 is a view of an input module for a catheter-based procedure system in accordance with some embodiments.

FIG. 6 is a view of input module 600 according to some embodiments. Input module 600 includes right-side controls 610 and left-side controls 620. Controls 611, 612, 613*a*, 613*b*, 614, 621, 622, 623*a*, 623*b*, and 624 may be implemented generally as described above with respect to similarly-numbered controls of input modules 400 and 500, although the physical profiles of controls 611, 614, 621 and 624 differ from their counterparts of input modules 400 and 500.

Knobs 611 and 621 may comprise a round or substantially round protrusion that extends upward from the flat base of input module 600. Each knob 611, 621 may include an integrated skirt 611*a*, 621*a* on which an operator's thumb may engage the knob during rotation thereof. Skirts 611*a* and 621*a* may include tactile surfaces to facilitate location and movement thereof. Knobs 611 and 621 may be located "centrally" with respect to buttons 615, 625, 614 and 624.

Each of buttons 613*a*, 613*b*, 623*a* and 623*b* may comprise a protrusion that extends upward from the base of module 600. Buttons 613*a*, 613*b*, 623*a* and 623*b* may extend upward from the base to a lesser degree than knobs 611 and 621. Buttons 613*a*, 613*b*, 623*a* and 623*b* may be triangular or any other shapes such as square, rectangular, oval, circular, etc.

Buttons 613*a* and 613*b* may be implemented using a single button capable of receiving two or more different inputs (e.g., a rocker button), and buttons 623*a* and 623*b* may also be implemented using such a single button. For example, buttons 613*a* and 613*b* may be implemented using a single button with one depressable end corresponding to button 613*a* and the other depressable end corresponding to button 613*b*. Buttons 613*a*, 613*b*, 623*a* and 623*b* may be parallel or substantially parallel to one other or may be arranged at an angle. Buttons 613*a*, 613*b*, 623*a* and 623*b* may be located "centrally" with respect to buttons 615, 625, 614 and 624.

Continuous activation buttons 614 and 624 may be substantially rectangular, as shown, rectangular, oval, circular or square. Continuous activation buttons 614 and 624 may be closer to an operator during operation than all other buttons and controls of module 600. Continuous activation buttons 614 and 524 may protrude from the base of module 600 or may be substantially flat and contiguous with the base of module 600.

Continuous activation buttons 614 and 624 may be smooth or textured (e.g., comprising raised portions such as dimples). Continuous activation buttons 614 and 624 may be physical buttons that deflect/translate when actuated, or solid-state buttons such as a capacitive touch panel or a piezoelectric device which are actuated by touch and do not noticeably "travel" when so activated.

Buttons 615 and 625 may be any shape such as squares, rectangles, ovals, etc. Buttons 615 and 625 may be located farther away from an operator during operation than all other buttons of module 600. Buttons 615 and 625 may protrude from the base of module 600 or be substantially contiguous therewith. Buttons 615 and 625 may be smooth or include raised portions such as dimples. The raised portions of various buttons 615 and 625 may differ from one another to assist an operator in distinguishing a button by touch alone.

In the embodiment shown in FIG. 6, controls 612 and 622 are wheels which include tactile elements to improve grip and to help an operator "find" these controls while not looking at the input module 600. In other embodiments, controls 612 and 622 are smooth. Controls 612 and 622 may be arranged parallel or substantially parallel to one another. Controls 612 and 622 may be located "centrally" on input module 600 with respect to buttons 615, 625, 614 and 624.

Input module 600 may be substantially flat over its entire surface or may comprise different elevations. For example, some portions of the surface may be raised with respect to others or may be lower with respect to others. A change in elevation may be gradual or sudden.

Right-side selection buttons 615 may be actuated to select one or more EMDs to be moved based on instructions issued in response to manipulation of right-side controls 610. Selection buttons 615 labeled 1, 2, 3 and W may be used to select, respectively, an EMD which is supported by a first cassette, an EMD which is supported by a second cassette, an EMD which is supported by a third cassette or to a guidewire. Selection buttons 615 may be used to simultaneously select more than one EMD at a given time (which may then be simultaneously controlled using right-side controls 610), and do not need to be continuously depressed by an operator to maintain such selection. Actuation of button 616, labeled X, causes de-selection of all EMDs currently-selected by selection buttons 615.

Figure 7:
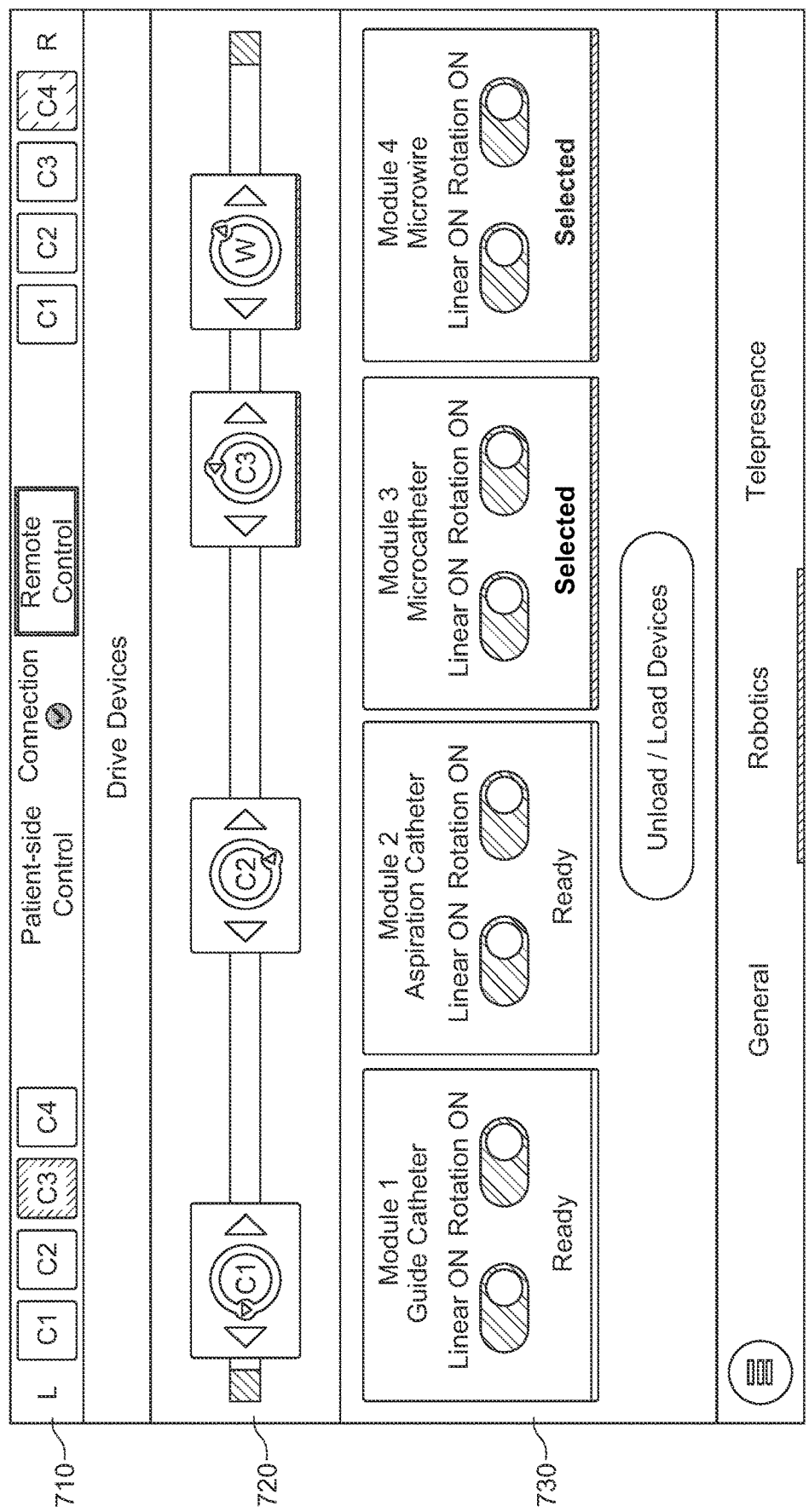
FIG. 7 is a view of a control station user interface for use in conjunction with an input module for a catheter-based procedure system in accordance with some embodiments.

FIG. 7 is a view of a user interface which may be presented to an operator of an input module during a procedure according to some embodiments. Section 710 of the user interface shows the one or more cassettes currently selected for the left-side controls (i.e., C3) and the one or more cassettes currently selected for the right-side controls (i.e., C4).

Figure 8:
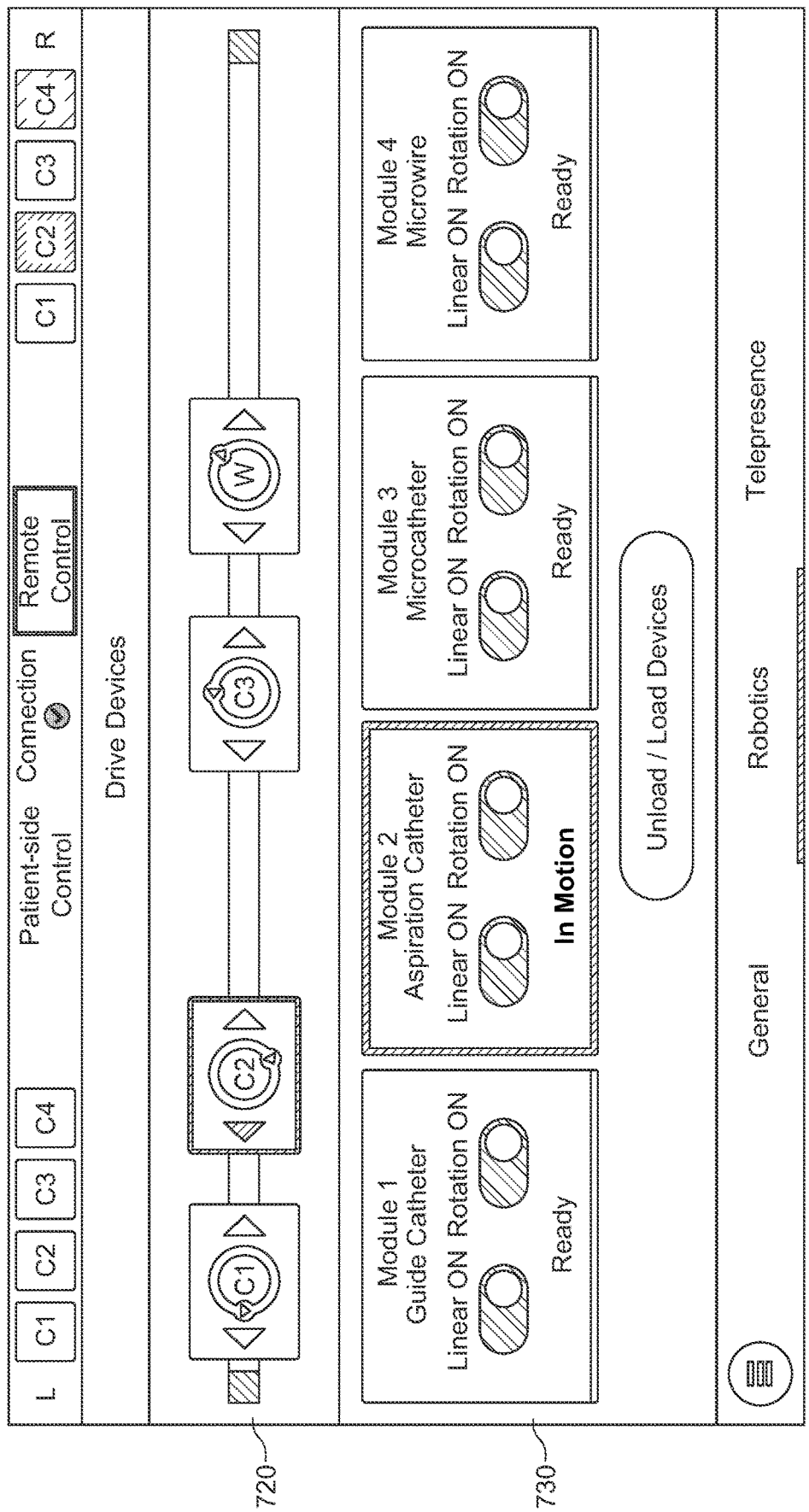
FIG. 8 is a view of a control station user interface for use in conjunction with an input module for a catheter-based procedure system in accordance with some embodiments.
Figure 9:
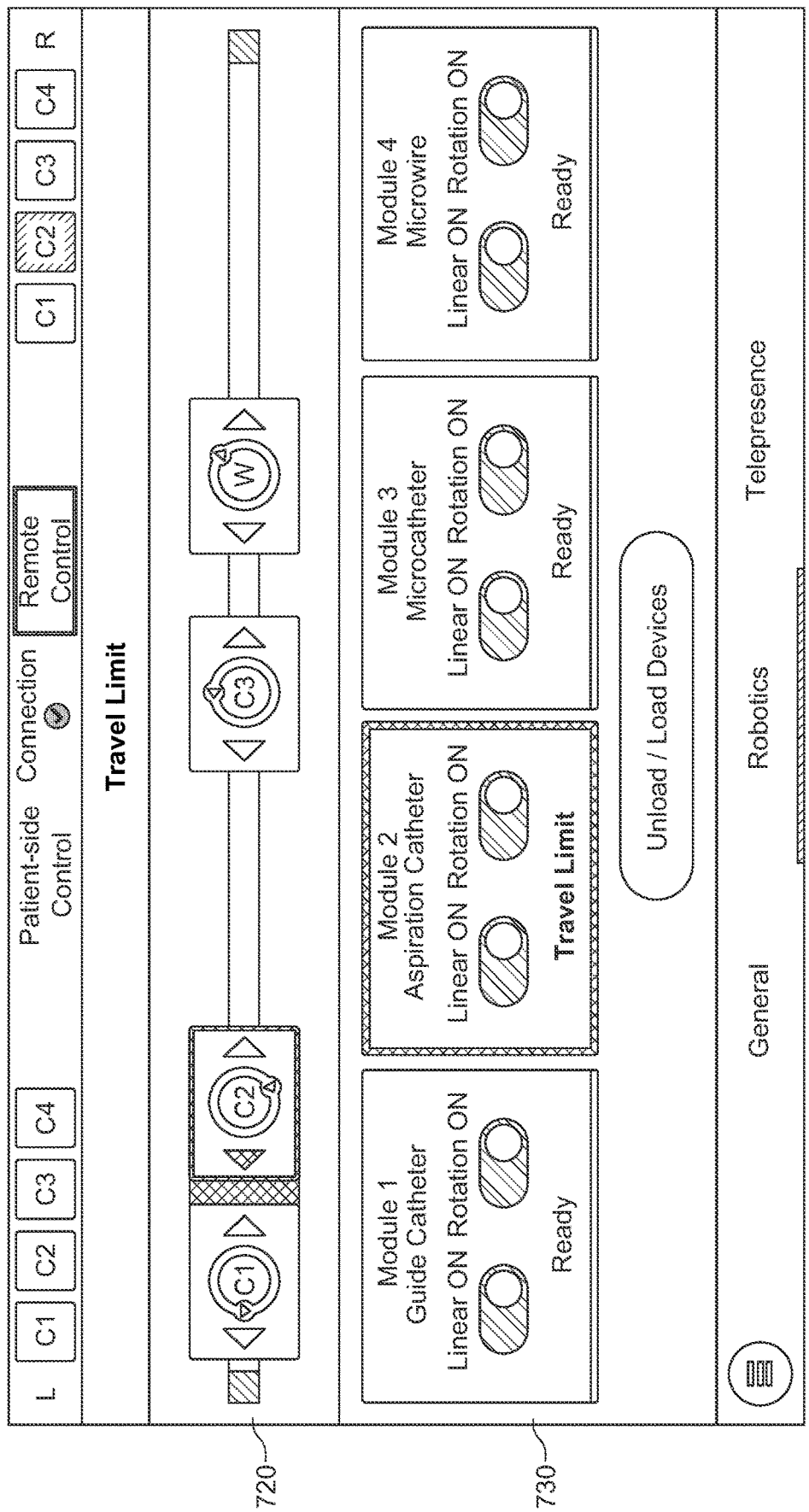
FIG. 9 is a view of a control station user interface for use in conjunction with an input module for a catheter-based procedure system in accordance with some embodiments.

Section 720 depicts the relative linear positions of each cassette as well as the rotational position of the EMD supported thereby. Section 730 identifies the EMD supported by each cassette (module). Section 720 and section 730 also indicate the cassettes which are currently selected. As shown in FIG. 8, during control of selected EMDs, section 720 depicts linear and rotational motion in near-real time and section 730 indicates that the selected EMDs are in motion. Furthermore, as shown in FIG. 9, sections 720 and 730 may both present a notification if a cassette has reached an end of its linear travel range.

Figure 10:
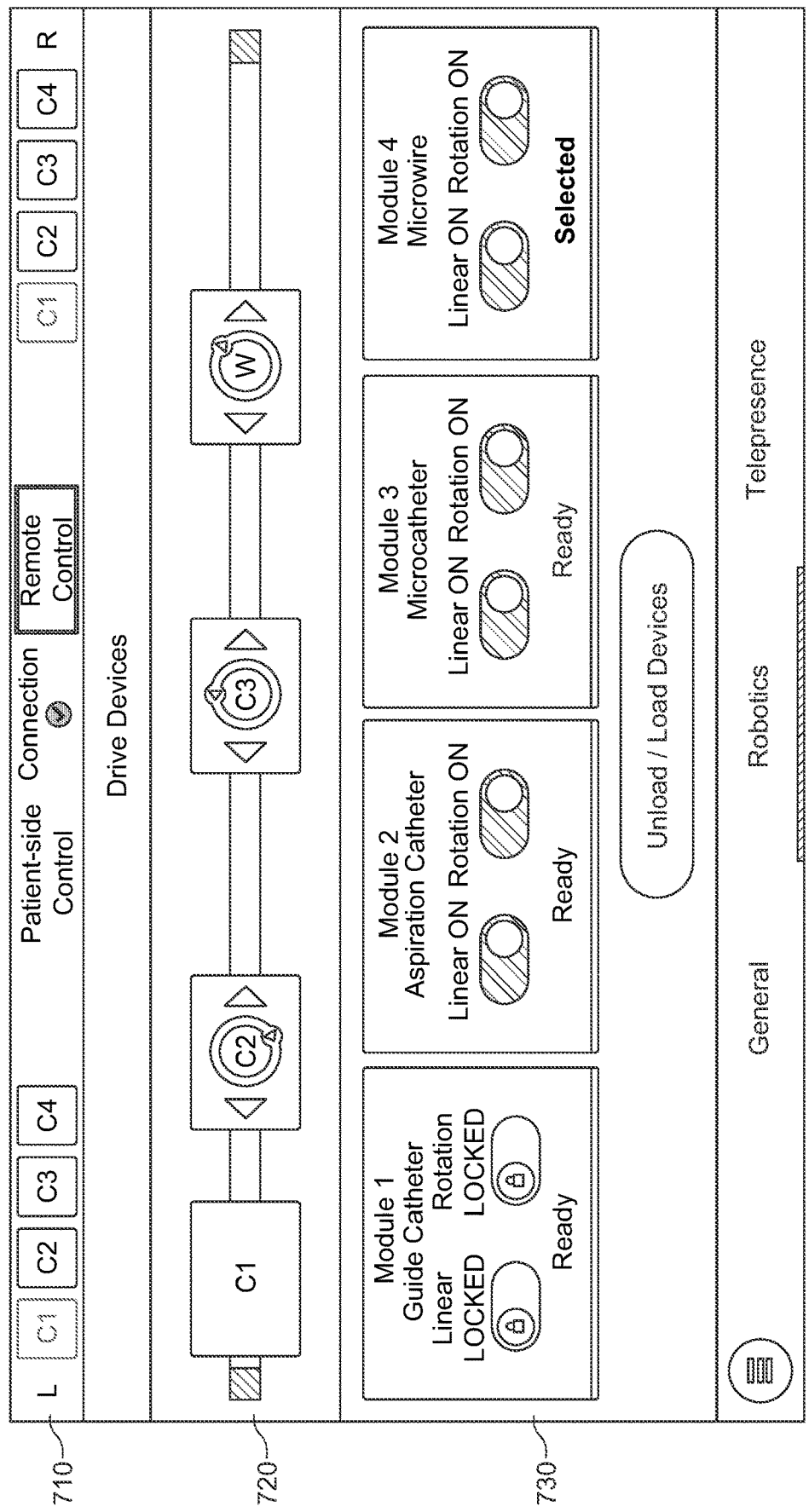
FIG. 10 is a view of a control station user interface for use in conjunction with an input module for a catheter-based procedure system in accordance with some embodiments.

FIG. 10 shows a user interface in which the operator has manipulated the switches of section 730 to lock linear and rotational motion of a guide catheter mounted in cassette 1. The operator may have slid the displayed switches of section 730 to the locked position using a finger or pointing device. Since linear and rotational motion are locked, both section 710 and section 720 of the user interface indicate that cassette 1 (i.e., C1) cannot be selected or moved.

According to some embodiments, a locked EMD will not move in the locked degree of freedom (rotational in the case of a rotation lock and linear in the case of a linear lock) even if the operator manipulates controls of the input module which would otherwise do so. Accordingly, the locks may be software-based in that commands which are contrary to the locks are blocked from receipt by the bedside unit. Embodiments may allow for operator-set rotational locks only, linear locks only, or both as shown in FIGS. 7-10.

In one example, an operator might activate a linear lock on a cassette so that the position of its EMD is not changed by the bedside technician while loading or unloading other devices during the course of the procedure. In this regard, it is common for the bedside technician to "jog" a cassette forward or backwards during EMD loading/unloading. The ability to lock linear movement allows the operator to control which cassettes are allowed to move during such loading/unloading.

Some EMDs, including microcatheters, sheaths, and stent retrievers, should not be rotated due to the potential for resulting damage. The rotation lock according to some embodiments could therefore beneficially prevent such an EMD from being rotated. Some EMDs, such as a balloon guide catheter, have a large hub with an extra tube that physically cannot rotate within a cassette, and a rotation lock may be used to prevent such rotation.

Rotation locks could be operator and/or system managed. For example, if a particular type of EMD is assigned to a cassette (as described below) and the system has been programmed with the knowledge that this type of device should not be rotated, the system may automatically activate a rotation lock on that cassette. The rotation lock may be partial, allowing the EMD to rotate a maximum of, for example +/−30 degrees. This lock may be overridden by the operator in some embodiments. In some embodiments, the operator cannot override the lock. For example, the user interface presents a rotation lock option (initially set to Off) only for those EMDs which may be rotated.

Figure 11:
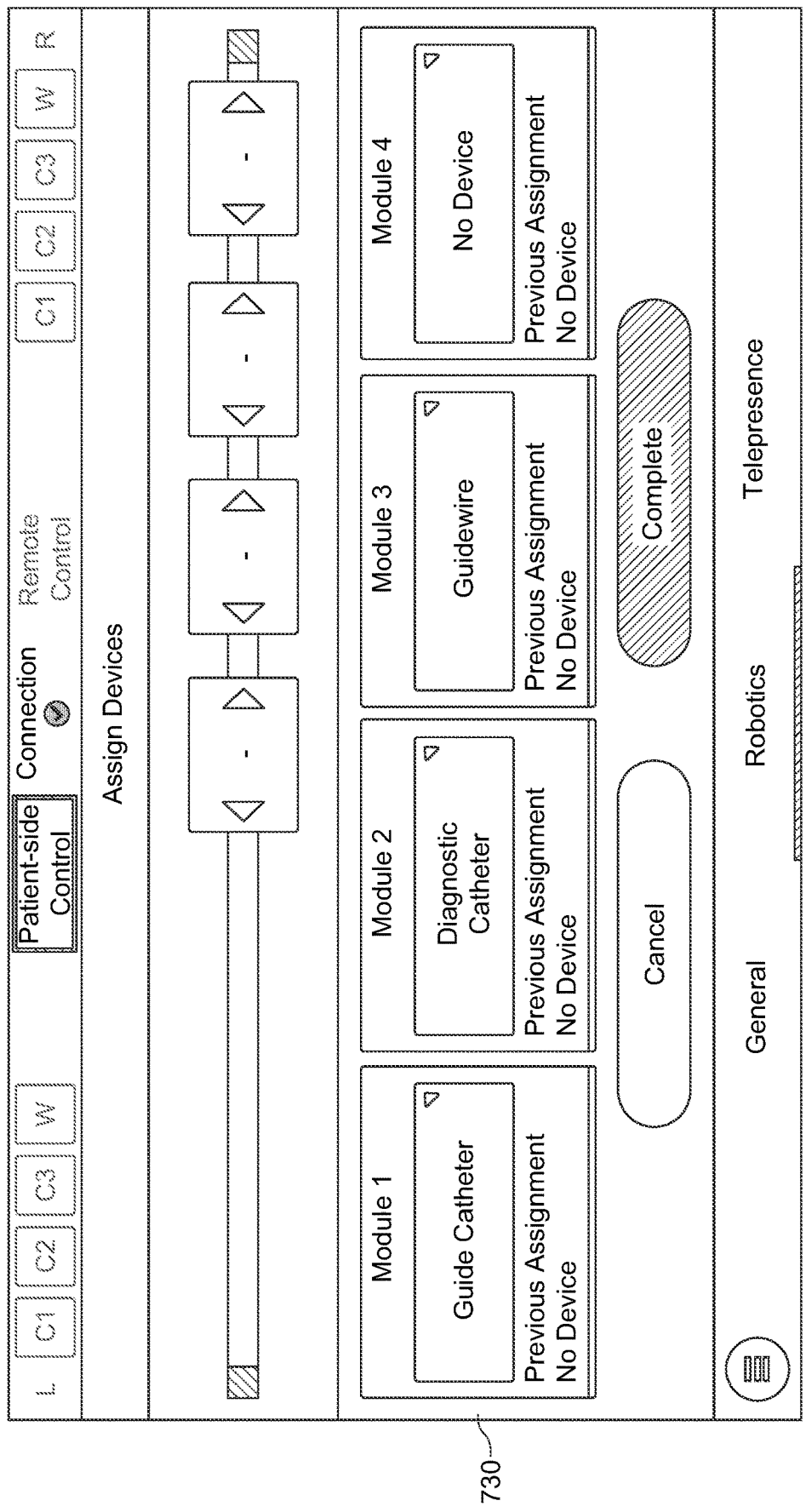
FIG. 11 is a view of a control station user interface for use in conjunction with an input module for a catheter-based procedure system in accordance with some embodiments.
Figure 12:
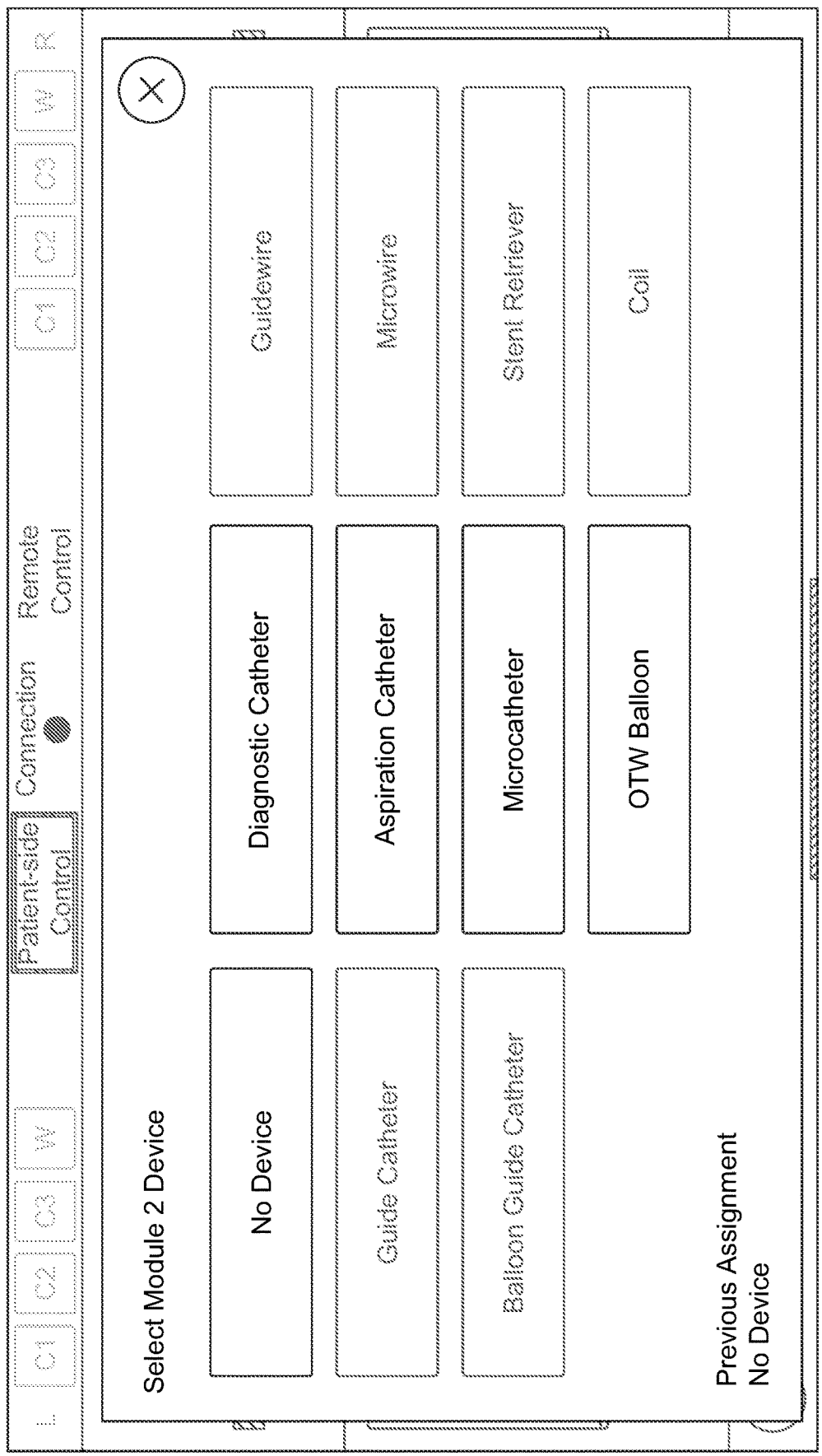
FIG. 12 is a view of a control station user interface for use in conjunction with an input module for a catheter-based procedure system in accordance with some embodiments.

FIG. 11 shows an interface for specifying the EMD supported by each respective cassette. The system may detect the type of EMDs loaded in each cassette and pre-populate the FIG. 11 interface in some embodiments. FIG. 12 may be presented upon selection of one of the cassettes (modules) of section 730. FIG. 12 allows the operator to select a type of EMD to be assigned to the selected cassette. According to some embodiments, the guidewire may be assigned to any cassette, and that cassette is then selected upon pressing the W button of the left-side or right-side controls of input module 600.

Computer-executable program code for controlling a catheter-based procedure system or presenting a user interface as described herein may be stored on non-transitory computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital versatile disks (DVD) or other optical storage, magnetic cassettes, magnetic tape, magnetic disk storage or other magnetic storage devices, or any other medium which can be used to store the desired instructions and which may be accessed by system 10 (shown in FIG. 1), including by internet or other computer network form of access.

What is claimed is:

1. A system for instructing a robotic drive to control two or more elongated medical devices (EMDs), the system comprising:

a first two or more selection buttons actuatable to cause selection of a first two or more EMDs;
a first control actuatable to cause issuance of an instruction to the robotic drive to simultaneously move each of the selected first two or more EMDs linearly;
a second control actuatable to cause issuance of an instruction to the robotic drive to simultaneously rotate each of the selected first two or more EMDs;
a second one or more selection buttons actuatable to cause selection of a second one or more EMDs while the first two or more EMDs remain selected; and
a third control actuatable to cause issuance of an instruction to simultaneously move each of the selected second one or more EMDs linearly while the selected first two or more EMDs remain selected.

2. The system according to claim 1, further comprising:
a fourth actuatable control; and
a fifth actuatable control,
wherein, while the fourth actuatable control is not actuated, actuation of the first control does not cause issuance of an instruction to simultaneously move each of the selected first two or more EMDs linearly, and actuation of the second control does not cause issuance of an instruction to simultaneously rotate each of the selected first two or more EMDs, and
wherein, while the fifth actuatable control is not actuated, actuation of the third control does not cause issuance of an instruction to simultaneously move each of the selected second one or more EMDs linearly while the selected first two or more EMDs remain selected.

3. The system according to claim 2, wherein the fourth actuatable control is actuatable by a heel of a palm of a first hand of an operator while the second control is actuatable by a thumb of the first hand and while the first control is actuatable by a finger of the first hand, and
wherein the fifth actuatable control is actuatable by the heel of a palm of a second hand of the operator while the third control is actuatable by a finger of the second hand.

4. The system according to claim 1, further comprising:
wherein, while the third actuatable control is not actuated, actuation of the first control does not cause issuance of an instruction to simultaneously move each of the selected first two or more EMDs linearly, and actuation of the second control does not cause issuance of an instruction to simultaneously rotate each of the selected first two or more EMDs.

5. The system according to claim 4, wherein the third actuatable control is actuatable by a heel of a palm of a hand while the second control is actuatable by a thumb of the hand.

6. The system according to claim 5, wherein the third actuatable control is actuatable by the heel of the palm of the hand while the first control is actuatable by a finger of the hand.

7. The system according to claim 1, further comprising:
a user interface including a first user interface control selectable to prevent linear motion of one of the selected first two or more EMDs; and
a processing unit to receive the instruction to simultaneously move each of the selected first two or more EMDs linearly, to determine, in response to receipt of the instruction, that the first user interface control is selected to prevent linear motion of the one of the selected first two or more EMDs, and, in response to the determination, to not instruct the robotic drive to simultaneously move each of the selected first two or more EMDs linearly in response to the instruction.

8. The system according to claim 1, further comprising:
a user interface including a first user interface control selectable to prevent rotational motion of one of the selected first two or more EMDs; and
a processing unit to receive the instruction to simultaneously rotate each of the selected first two or more EMDs, to determine, in response to receipt of the instruction, that the first user interface control is selected to prevent rotational motion of the one of the selected first two or more EMDs, and, in response to the determination, to not instruct the robotic drive to simultaneously rotate each of the selected first two or more EMDs in response to the instruction.

9. The system according to claim 8,
the user interface including a second user interface control selectable to prevent linear motion of one of the selected first two or more EMDs, and
the processing unit to receive the instruction to simultaneously move each of the selected first two or more EMDs linearly, to determine, in response to receipt of the instruction, that the second user interface control is selected to prevent linear motion of the one of the selected first two or more EMDs, and, in response to the determination, to not instruct the robotic drive to simultaneously move each of the selected first two or more EMDs linearly in response to the instruction.

10. A system comprising:
a robotic drive comprising a plurality of cassettes, each cassette to move an elongated medical device (EMD) loaded therein; and
an input module comprising:
a first two or more selection buttons actuatable to cause selection of a first two or more EMDs loaded in respective ones of the plurality of cassettes;
a second one or more selection buttons actuatable to cause selection of a second one or more EMDs loaded in respective ones of the plurality of cassettes while the selected first two or more EMDs remain selected;
a first control actuatable to cause issuance of an instruction to the robotic drive to simultaneously move each of the selected first two or more EMDs linearly;
a second control actuatable to cause issuance of an instruction to the robotic drive to simultaneously rotate each of the selected first two or more EMDs; and
a third control actuatable to cause issuance of an instruction to the robotic drive to simultaneously move each of the selected second one or more EMDs linearly while the first two or more EMDs remain selected.

11. The system according to claim 10, the input module further comprising:
a fourth control actuatable to cause issuance of an instruction to the robotic drive to simultaneously rotate each of the selected second one or more EMDs while the first two or more EMDs remain selected.

12. The system according to claim 11, the input module further comprising:
a fifth actuatable control; and
a sixth actuatable control,
wherein, while the fifth actuatable control is not actuated, actuation of the first control does not cause issuance of an instruction to simultaneously move each of the selected first two or more EMDs linearly, and actuation of the second control does not cause issuance of an instruction to simultaneously rotate each of the selected first two or more EMDs, and wherein, while the sixth actuatable control is not actuated, actuation of the third control does not cause issuance of an instruction to simultaneously move each of the selected second one or more EMDs linearly while the selected first two or more EMDs remain selected, and actuation of the fourth control does not cause issuance of an instruction to simultaneously rotate each of the selected second one or more EMDs while the selected first two or more EMDs remain selected.

13. The system according to claim 12, wherein the fifth actuatable control is actuatable by a heel of a palm of a first hand of an operator while the second control is actuatable by a thumb of the first hand and while the first control is actuatable by a finger of the first hand, and
wherein the sixth actuatable control is actuatable by the heel of a palm of a second hand of the operator while the fourth control is actuatable by a thumb of the second hand and while the third control is actuatable by a finger of the second hand.

14. The system according to claim 10,
wherein, while the third actuatable control is not actuated, actuation of the first control does not cause issuance of an instruction to simultaneously move each of the selected first two or more EMDs linearly, and actuation of the second control does not cause issuance of an instruction to simultaneously rotate each of the selected first two or more EMDs,
wherein the third actuatable control is actuatable by a heel of a palm of a hand while the second control is actuatable by a thumb of the hand, and
wherein the third actuatable control is actuatable by the heel of the palm of the hand while the first control is actuatable by a finger of the hand.

15. The system according to claim 10, further comprising:
a user interface including a first user interface control selectable to prevent rotational motion of one of the selected first two or more EMDs; and
a processing unit to receive the instruction to simultaneously rotate each of the selected first two or more EMDs, to determine, in response to receipt of the instruction, that the first user interface control is selected to prevent rotational motion of the one of the selected first two or more EMDs, and, in response to the determination, to not instruct the robotic drive to simultaneously rotate each of the selected first two or more EMDs in response to the instruction.

16. The system according to claim 15, further comprising:
the user interface including a second user interface control selectable to prevent linear motion of one of the selected first two or more EMDs; and
a processing unit to receive the instruction to simultaneously move each of the selected first two or more EMDs linearly, to determine, in response to receipt of the instruction, that the second user interface control is selected to prevent linear motion of the one of the selected first two or more EMDs, and, in response to the determination, to not instruct the robotic drive to simultaneously move each of the selected first two or more EMDs linearly in response to the instruction.

17. A method comprising:
detecting actuation of a first two or more selection buttons actuatable to cause selection of a first two or more elongated medical devices (EMDs);
detecting actuation of a second one or more selection buttons actuatable to cause selection of a second one or more EMDs;
detecting actuation of a first control;
in response to the actuation of the first control, issuing an instruction to simultaneously move each of the selected first two or more EMDs linearly;
detecting actuation of a second control;
in response to the actuation of the second control, issuing an instruction to simultaneously rotate each of the selected first two or more EMDs
detecting actuation of a third control; and
in response to the actuation of the third control, issuing an instruction to simultaneously move each of the selected second one or more EMDs linearly while the first two or more EMDs remain selected.

18. The method according to claim 17, further comprising:
detecting actuation of a fourth control; and
in response to the actuation of the fourth control, issuing an instruction to simultaneously rotate each of the selected second one or more EMDs while the selected first two or more EMDs remain selected.

19. The method according to claim 18, further comprising:
detecting actuation of a fifth actuatable control; and
detecting actuation of a sixth actuatable control,
wherein issuance of the instruction to simultaneously move each of the selected first two or more EMDs linearly is in response to the actuation of the first control and the actuation of the fifth actuatable control,
wherein issuance of the instruction to simultaneously rotate each of the selected first two or more EMDs is in response to the actuation of the second control and the actuation of the fifth actuatable control,
wherein issuance of the instruction to simultaneously move each of the selected second one or more EMDs linearly is in response to the actuation of the third control and the actuation of the sixth actuatable control, and
wherein issuance of the instruction to simultaneously rotate each of the selected second one or more EMDs is in response to the actuation of the fourth control and the actuation of the sixth actuatable control.

* * * * *